United States Patent
Roberson et al.

(10) Patent No.: US 10,650,228 B2
(45) Date of Patent: May 12, 2020

(54) DEVICES AND METHODS FOR ANALYZING ANIMAL BEHAVIOR

(71) Applicants: Children's Medical Center Corporation, Boston, MA (US); President and Fellows of Harvard College, Cambridge, MA (US)

(72) Inventors: David P. Roberson, Cambridge, MA (US); Clifford J. Woolf, Newton, MA (US); Michael T. Do, Brookline, MA (US); Alexander B. Wiltschko, Brookline, MA (US); Sandeep Robert Datta, Newton, MA (US)

(73) Assignees: Children's Medical Center Corporation, Boston, MA (US); President and Fellows of Harvard College, Cambridge, MA (US)

( * ) Notice: Subject to any disclaimer, the term of this patent is extended or adjusted under 35 U.S.C. 154(b) by 55 days.

(21) Appl. No.: 15/760,792

(22) PCT Filed: Sep. 16, 2016

(86) PCT No.: PCT/US2016/052359
§ 371 (c)(1),
(2) Date: Mar. 16, 2018

(87) PCT Pub. No.: WO2017/049249
PCT Pub. Date: Mar. 23, 2017

(65) Prior Publication Data
US 2019/0080158 A1    Mar. 14, 2019

Related U.S. Application Data

(60) Provisional application No. 62/220,924, filed on Sep. 18, 2015.

(51) Int. Cl.
*G06K 9/20* (2006.01)
*A01K 1/03* (2006.01)
(Continued)

(52) U.S. Cl.
CPC .......... *G06K 9/00348* (2013.01); *A01K 1/031* (2013.01); *A01K 29/005* (2013.01);
(Continued)

(58) Field of Classification Search
None
See application file for complete search history.

(56) References Cited

U.S. PATENT DOCUMENTS 3,974,798 A    8/1976  Meetze, Jr.
4,574,734 A    3/1986  Mandalaywala et al.
(Continued)

FOREIGN PATENT DOCUMENTS

CA    2928972 A1    5/2015
CN    201019748 Y    2/2008
(Continued)

OTHER PUBLICATIONS

International Search Report and Written Opinion for International Application No. PCT/US2016/052359, dated Nov. 18, 2016.
(Continued)

*Primary Examiner* — Idowu O Osifade
(74) *Attorney, Agent, or Firm* — Wolf, Greenfield & Sacks, P.C.

(57) ABSTRACT

A device for detecting and recording animal behavior is provided. The device includes at least one corral that defines a contained field, the base surface of the at least one corral being sensitive to the animal's footprint. The device also includes an image capturing device that cooperates with the base surface to capture a first video frame in which at least one of a tail, body and head of the animal is illuminated by
(Continued)

a light below the animal and a second video frame in which both a profile of a full footprint and a profile of a toe print of the animal when the animal is standing on its toes is illuminated by a light that is totally internally reflected within the base surface. A control system is arranged to control the image capturing device to capture the first and second video frames.

25 Claims, 26 Drawing Sheets

(51) Int. Cl.
*A01K 29/00* (2006.01)
*G06K 9/00* (2006.01)
*A61B 5/00* (2006.01)
*A61B 5/11* (2006.01)
*A61B 5/16* (2006.01)

(52) U.S. Cl.
CPC .......... *A61B 5/0077* (2013.01); *A61B 5/1118* (2013.01); *G06K 9/00335* (2013.01); *G06K 9/00362* (2013.01); *G06K 9/209* (2013.01); *G06K 9/2027* (2013.01); *G06K 9/2036* (2013.01); *A61B 5/112* (2013.01); *A61B 5/1113* (2013.01); *A61B 5/165* (2013.01); *A61B 5/4824* (2013.01); *A61B 5/7267* (2013.01); *A61B 2503/40* (2013.01)

(56) References Cited

U.S. PATENT DOCUMENTS

| | | | |
|---|---|---|---|
| 4,858,621 | A | 8/1989 | Franks |
| 4,968,974 | A | 11/1990 | Sakano |
| 6,678,413 | B1 | 1/2004 | Liang et al. |
| 7,044,082 | B1 | 5/2006 | Hewett et al. |
| 7,068,842 | B2 | 6/2006 | Liang et al. |
| 8,514,236 | B2 | 8/2013 | Kobla et al. |
| 8,634,635 | B2 | 1/2014 | Bai et al. |
| 10,238,085 | B2 | 3/2019 | Woolf et al. |
| 2003/0004652 | A1 | 1/2003 | Brunner et al. |
| 2003/0055362 | A1 | 3/2003 | Hampton |
| 2003/0206287 | A1 | 11/2003 | McClurg et al. |
| 2005/0163349 | A1 | 7/2005 | Brunner et al. |
| 2006/0107066 | A1 | 5/2006 | Cova et al. |
| 2007/0021421 | A1 | 1/2007 | Hampton |
| 2010/0111359 | A1 | 5/2010 | Bai et al. |
| 2010/0143265 | A1* | 6/2010 | Hewes ............... A01N 25/16 424/43 |
| 2010/0175629 | A1 | 7/2010 | Garmon |
| 2010/0217157 | A1 | 8/2010 | Tasch |
| 2010/0246902 | A1 | 9/2010 | Rowe et al. |
| 2010/0317094 | A1* | 12/2010 | Ricco ............... G01N 33/04 435/287.2 |
| 2012/0180731 | A1 | 7/2012 | Garner et al. |
| 2012/0293631 | A1 | 11/2012 | Schwarz et al. |
| 2014/0251228 | A1 | 9/2014 | Jensen-Jarolim et al. |
| 2016/0150758 | A1 | 6/2016 | Salem et al. |
| 2016/0270364 | A1 | 9/2016 | Woolf et al. |
| 2016/0300123 | A1 | 10/2016 | Jewell et al. |
| 2017/0064929 | A1 | 3/2017 | Yakovenko |
| 2017/0111128 | A1 | 4/2017 | Hammerschmidt |
| 2017/0351898 | A1 | 12/2017 | Zhang |
| 2018/0260645 | A1 | 9/2018 | Roberson et al. |

FOREIGN PATENT DOCUMENTS

| | | |
|---|---|---|
| WO | WO 03/025615 A2 | 3/2003 |
| WO | WO 2005/001768 A1 | 1/2005 |
| WO | WO 2007/071572 A1 | 6/2007 |

OTHER PUBLICATIONS

International Preliminary Report on Patentability for International Application No. PCT/US2016/052359, dated Mar. 29, 2018.

[No Author Listed] Automatic Footprint Classification. Noldus. Last Accessed on Oct. 24, 2013 at http://www.noldus.com/CatWalk-XT/automatic-footprint-classification 1 page.

[No Author Listed] Behavioral Research Blog—CatWalk gait analysis versus treadmills. Noldus. http://info.noldus.com/bid/93553/CatWalk-gait-analysis-versus-treadmills; Retrieved from the WayBack Machine on Aug. 29, 2016, noting date of May 13, 2013. 2 pages.

[No Author Listed] CatWalk 7.1 versus CatWalk XT. Noldus. http://www.noldus.com/catwalk-71-versus-catwalk-xt-81; Retrieved from the WayBack Machine on Aug. 29, 2016, noting date of Oct. 24, 2013. 2 pages.

[No Author Listed] CatWalktmXT. Noldus. Last Accessed on Oct. 24, 2013 at http://www.noldus.com/animal-behavior-research/products/catwalk 2 pages.

[No Author Listed] Discover CatWalk XT. Noldus. http://www.noldus.com/CatWalk-XT/specifications#; Retrieved from the WayBack Machine on Aug. 29, 2016, noting date of Oct. 24, 2013. 3 pages.

[No Author Listed] Illuminated Footprints Technology. http://www.noldus.com/CatWalk-XT/illuminated-footprints-technology; Retrieved from the WayBack Machine on Aug. 29, 2016, noting archive date of Oct. 24, 2013. 1 page.

[No Author Listed] New! CatWalk XT 10.5. Noldus. http://www.noldus.com/CatWalk-XT/new-features; Retrieved from the WayBack Machine on Aug. 29, 2016, noting date of Oct. 24, 2013. 4 pages.

[No Author Listed] Noldus—List of publications. Last Accessed on Oct. 24, 2013 at http://www.noldus.com/content/list-publications 3 pages.

Angeby-Möller et al., Using the CatWalk method to assess weight-bearing and pain behaviour in walking rats with ankle joint monoarthritis induced by carrageenan: effects of morphine and rofecoxib. J Neurosci Methods. Sep. 15, 2008;174(1):1-9. doi: 10.1016/j.jneumeth.2008.06.017.

Betts et al., A device for measuring plantar pressures under the sole of the foot. IMechE. 1978;7(4):223-8.

Koopmans, CatWalk: the next step in gait analysis. Noldus. http://www.noldus.com/documentation/80; Retrieved from the WayBack Machine on Aug. 29, 2016, noting date of Oct. 24, 2013. 2 pages.

Roedel et al., Effects of light or dark phase testing on behavioural and cognitive performance in DBA mice. Lab Anim. 2005;40:371-81.

Vrinten et al., 'CatWalk' automated quantitative gait analysis as a novel method to assess mechanical allodynia in the rat; a comparison with von Frey testing. Pain. Mar. 2003;102(1-2):203-9.

Extended European Search Report for European Application No. 16847509.3, dated Apr. 4, 2019.

U.S. Appl. No. 15/032,730, filed Apr. 28, 2016, Woolf et al.
U.S. Appl. No. 15/760,768, filed Mar. 16, 2018, Roberson et al.
PCT/US2016/052359, Nov. 18, 2016, International Search Report and Written Opinion.
PCT/US2016/052359, Mar. 29, 2018, International Preliminary Report on Patentability.

* cited by examiner

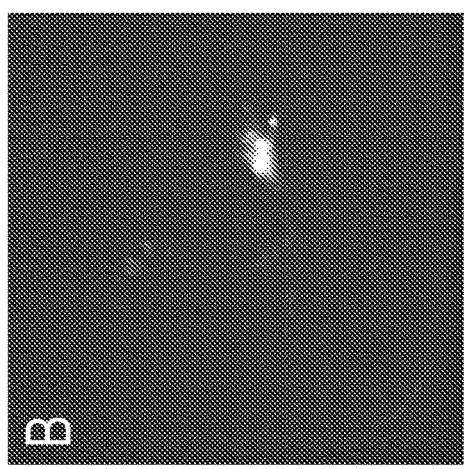
FIG. 11A
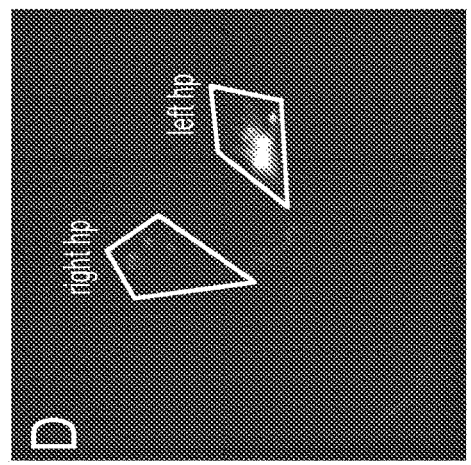
FIG. 11B
FIG. 11C
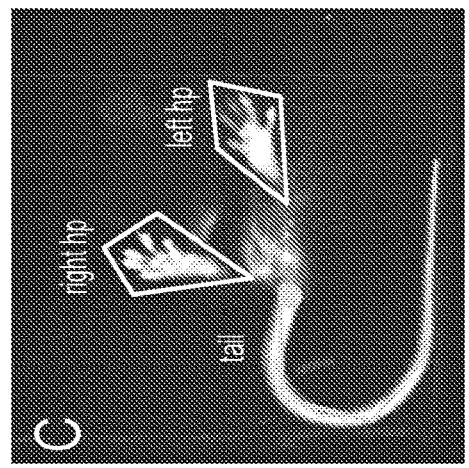
FIG. 11D

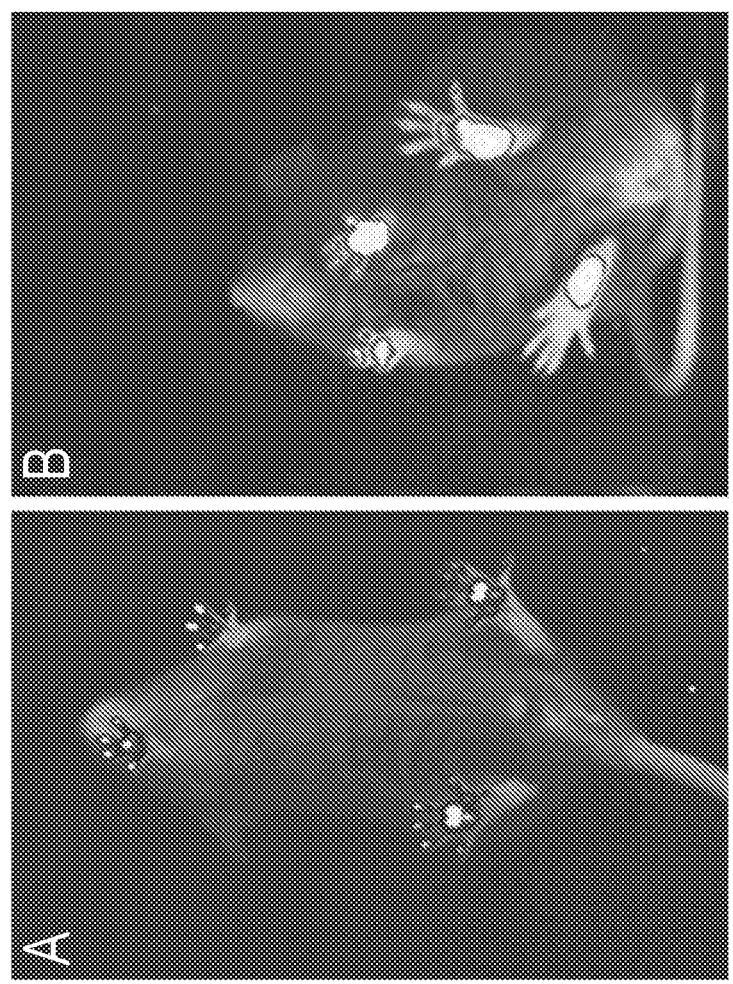

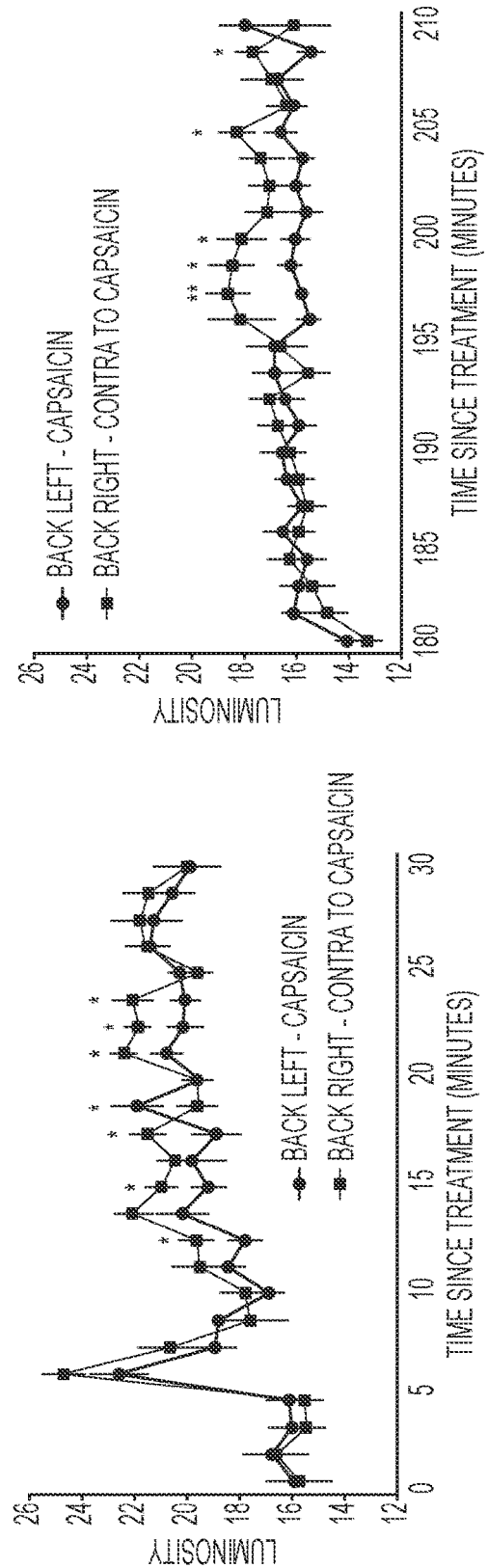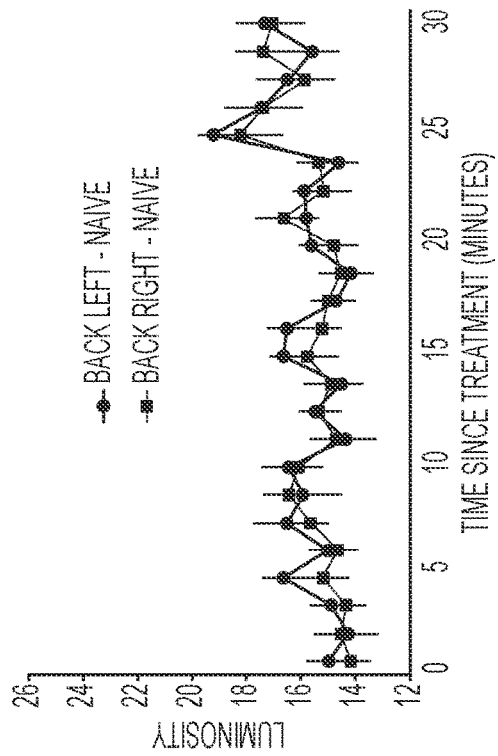
FIG. 14A
FIG. 14B
FIG. 14C

DEVICES AND METHODS FOR ANALYZING ANIMAL BEHAVIOR

CROSS-REFERENCE TO RELATED APPLICATIONS

This application is a national stage filing under 35 U.S.C. § 371 of international applciation PCT/US2016/052359, filed Sep. 16, 2016, which claims the benefit under 35 U.S.C. § 119(e) to U.S. Provisional Application Ser. No. 62/220,924, entitled "DEVICES AND METHODS FOR ANALYZING RODENT BEHAVIOR," filed on Sep. 18, 2015, each of which is herein incorporated by reference in its entirety.

FEDERALLY SPONSORED RESEARCH

This invention was made with U.S. Government support under Grant Nos. F31 NS084716-02, each awarded by the National Institute of Health. The Government has certain rights in this invention.

FIELD

Devices and methods for analyzing animal behavior are disclosed.

BACKGROUND

Animal behavior detection and analysis may be a useful experimental tool, for example, to determine whether a certain medication, stimulus or environment has a consequence on the animal's behavior. Such information can be useful in developing treatments for use in other animals, including humans. Such a tool also may be used for diagnostic purposes, for example, to identify a physical ailment in an animal, such as a human.

SUMMARY

Devices and methods for acquisition and analysis of animal behaviors are disclosed. Aspects disclosed herein relate to devices and methods that image the inferior surfaces (e.g., the plantar surface of paws, and inferior body parts) of freely behaving laboratory rodents in lit or dark conditions. This enables the identification and analysis of locomotion, gait, touch and pressure contact, behaviors related to nerve injury and regeneration, pain-like behavior, scratching, anxiety, aggression, social interaction, etc., of freely behaving rodents including mice and rats, either individually or in groups, and either in lit or dark environments. Conditions are observed via changes in the spatial extent, intensity and timing of the contact area of animal footpads and its relation to the rest of the body of the animal.

According to one aspect, a device for detecting and recording animal behavior is disclosed. The device includes at least one corral defining a contained field. A base surface of the at least one corral is sensitive to a footprint of the animal. An image capturing device cooperates with the base surface to capture both a profile of a full footprint of the animal (e.g., extent and intensity) and a profile of a toe print of a freely-behaving animal when the animal is standing on its toes, heels or footpads as well as by lighting the background or foreground to separately identify the position of the whole animal.

According to another aspect, a device for detecting and recording animal behavior is disclosed. The device includes a transparent base surface being sensitive to a footprint of the animal and an image capturing device beneath the base surface to capture both an image of a full footprint of the animal and an image of a toe print of the animal when the animal is standing on its toes. The device is adapted to provide a stimulus to the animal (e.g., by targeting light at the point of contact with the surface).

According to yet another aspect, a method of collecting behavioral information of a group of animals is disclosed. At least a subset of the group of animals is in a corral and is isolated from another subset of the group of animals. The method includes stimulating a first animal with a stimulus and observing a resulting behavior of the first animal via imaging both a footprint and a toe print of the first animal in response to the stimulus (e.g., imaging the spatial extent, pressure-related footprint intensity or timing of both the footprint and the toe print of the first animal). In some embodiments, the stimulus may include placing at least a subset of rodents in the same corral and observing the social interactions amongst the subset of rodents.

According to still another embodiment, a device for detecting and recording animal behavior is disclosed. The device includes at least one corral defining a contained field, a base surface of the at least one corral being sensitive to a footprint of the animal and an image capturing device cooperating with the base surface to capture both a profile of a full footprint of the animal and a profile of a toe print of the animal when the animal is standing on its toes. A first light is totally internally reflected within the base surface. A second light illuminates at least one of a tail, body and head of the animal from below the animal. In some embodiments, first and second light sources produce the first and second lights, respectively. In other embodiments, a first light source produces the first and second lights.

According to yet another embodiment, a method of collecting behavior information of an animal is disclosed. The method includes capturing a first image of at least one of a head, body and tail of the animal when the animal is illuminated with a first light, and capturing a second image of both a profile of a full footprint of the animal and a profile of a toe print of the animal when a second light is totally internally reflected within the base surface to generate evanescent light between the footprint and the toe print of the animal and the base surface.

According to still another embodiment, a device for detecting and recording animal behavior is disclosed. The device includes at least one corral defining a contained field, a base surface of the at least one corral being sensitive to a footprint of the animal, an image capturing device cooperating with the base surface to capture a first video frame in which at least one of a tail, body and head of the animal is illuminated by a light below the animal and a second video frame in which both a profile of a full footprint of the animal and a profile of a toe print of the animal when the animal is standing on its toes is illuminated by a light that is totally internally reflected within the base surface, and a control system arranged to control the image capturing device to capture the first and second video frames, the control system being further arranged to identify a paw in the first video frame and measure a corresponding luminance of the identified paw in the second frame.

According to another embodiment, a method of collecting behavior information of an animal is disclosed. The method includes capturing a first image of at least one of a head, body and tail of the animal when the animal is illuminated with a first light, capturing a second image of both a profile of a full footprint of the animal and a profile of a toe print of the animal when a second light is totally internally reflected within the base surface to generate evanescent light between the footprint and the toe print of the animal and the base surface, identifying a first footprint in the first image; and measuring a corresponding evanescent light generated between the identified first footprint and the base surface in the second image.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 11A-11B are images representing screen shots of paired videos captured with a capturing device, the first showing the identity and position of features of an animal and the second showing the contact area of those features;

FIGS. 11C-11D are machine vision algorithms that analyze the frames of FIGS. 11A and 11B, respectively;

FIGS. 12A-12B are images representing screen shots of paired videos captured with a capturing device, the first showing the identity and position of features of an animal and the second showing the contact area of those features;

FIGS. 14A-C illustrate automated score of luminesce of left and right hind paws of freely behaving rodents;

DETAILED DESCRIPTION

Figure 1:
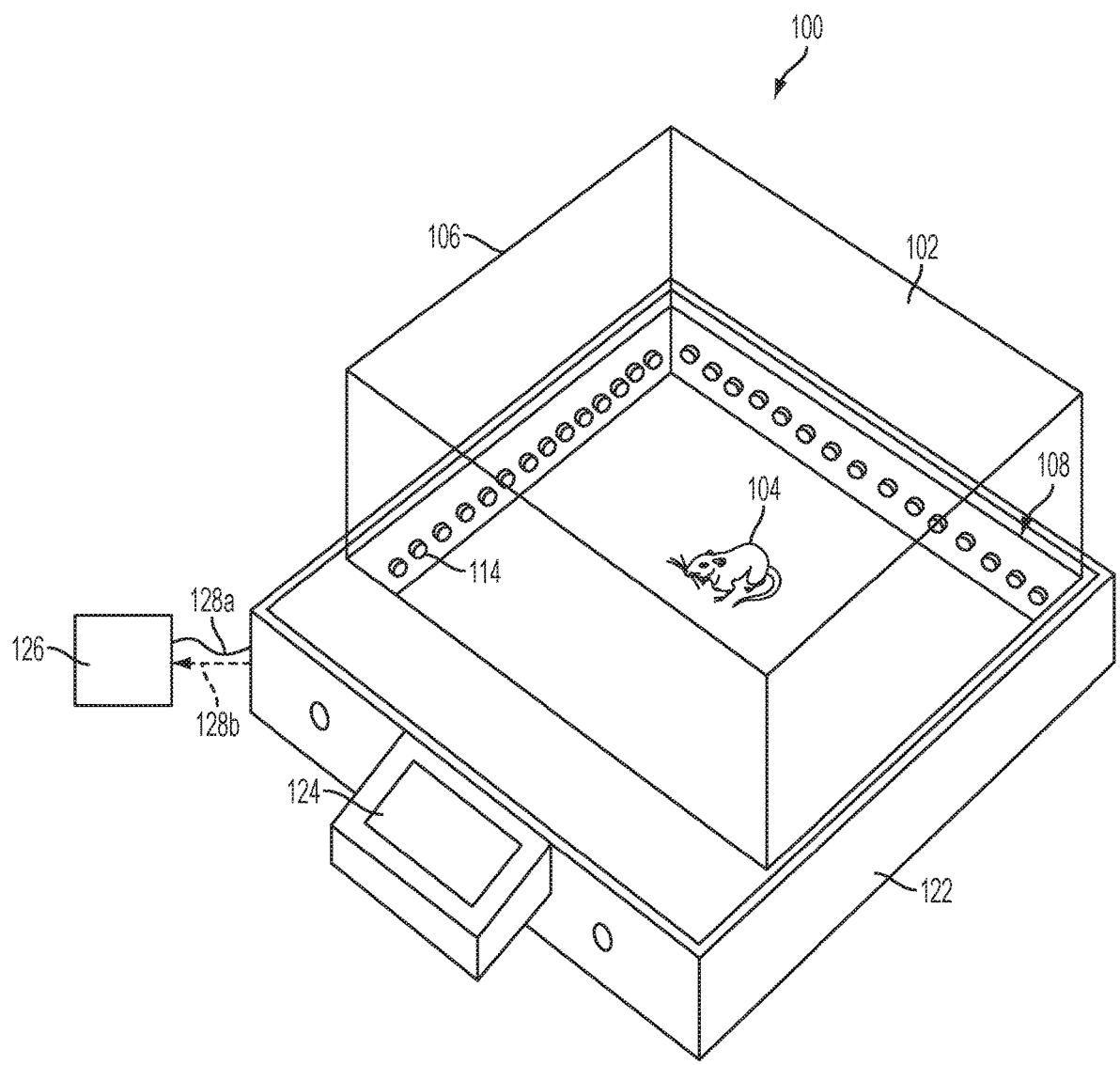
FIG. 1 is a perspective view of a device for monitoring animal behavior according to one embodiment.

Valuable information can be learned for laboratory studies by monitoring and analyzing the activity and motor performance of animals, e.g. rodents. One such application is the identification and analysis of locomotion, gait, touch and pressure against surfaces, nerve injury and regeneration, pain-like behavior, itch-like behavior, anxiety, aggression, and/or social interaction of the rodents. For example, identifying characteristic changes in gait that may accompany reactions to certain stimuli. Applicants have recognized that by monitoring the activity of freely behaving rodents, either individually or in groups, advantages may be realized. In some embodiments, the behavior of rodents is monitored after the rodents have been genetically modified and/or after the rodents are subjected to different types of stimulus in lit or dark environments.

According to one aspect, the voluntary and evoked movement of freely behaving animals, such as rodents, e.g., mice or rats, is monitored via a device capable of producing images of topographic features representing an inferior surface of the freely behaving animal. In some embodiments, this includes the spatial extent, intensity and dynamic changes of the surface. The inferior surface of the rodents may include a paw print, a toe print, or any other suitable inferior surface of the animal, e.g., a rodents' abdomen or tail. Without wishing to be bound by theory, freely behaving animals may include animals that are allowed to travel without obstruction within an area, such as a corral. It should be noted that such corral is not limited to an outdoor area for large animals; rather, as contemplated herein, a corral can be a test chamber for use with small animals, such as rodents (e.g., mice or rats).

In some embodiments, the device utilizes a horizontal contact sensor positioned above a capturing device, such as a video camera. In some embodiments, the contact sensor is a horizontal, transparent sensor. During experimentation, the subject animal may be contained within an open-bottom chamber and placed directly on top of the sensor, thus permitting the animal to roam freely on top of the sensor while being video recorded from below.

The sensor may be constructed based on the phenomenon of frustrated total internal reflection (FTIR) of band light. In some embodiments, the sensor is constructed based on FTIR of a non-visible band light, such as near-infrared, infrared, or ultraviolet light, although other suitable band light may be employed as this aspect of the disclosure is not limited in this regard. In one embodiment, the contact sensor includes a horizontally-positioned transparent glass or acrylic panel with a light source in the non-visible range. For example, infrared LED lights may be positioned around the perimeter of the panel (e.g., as strip lights or as lights mounted in a channel of a removable rail). Without wishing to be bound by theory, when the light strikes the medium boundary between the glass panel and the ambient air above the panel at an angle larger than the critical angle, the light is totally internally reflected and no light is emitted towards the camera below. Again, without wishing to be bound by theory, when an object, such as a mouse paw pad, having a higher refractive index than air comes within several wavelengths distance of the glass/air boundary, the evanescent wave passes light energy into the object, making it visible to the camera below. Stated another way, when the object, e.g. the mouse paw, comes into contact with the panel, the evanescent light field generated by the internally reflected light is "frustrated" and refracted out of the glass panel where it can be detected by a camera positioned below the glass panel. In some embodiments, the intensity, contact area, spatial extent and position of the "frustrated" light signal and its change over time facilitates determining the physical and physiological aspects of the animal's behavior, such as the relative weight borne on each paw or the distribution of weight within each footprint. This, in turn, may provide an objective readout relating to the subjective experience of the animal.

In some embodiments, the non-visible band light facilitates monitoring of nocturnal behavior during the nighttime period when rodents are most active. Without wishing to be bound by theory, as the light is not visible to the animals, the animals are undisturbed, unless subjected to a stimulus, and thus are left to roam freely.

To facilitate observation of nocturnal behavior, the open-bottomed chamber may be made of an opaque material and the chamber area illuminated from a light source positioned under the panel or sensor using red, near-infrared or other lighting that is not visible to rodents. Similarly, a visible light source positioned beneath the sensor or panel may be used to illuminate the inferior surfaces of the animal that are not in contact with the sensor.

In other embodiments, the device is configured to deliver different types of stimulus to the freely roaming rodents and to examine the rodents' behavioral responses after application of the stimulus. In some embodiments, the stimulus includes thermal, mechanical, electric, audio, olfactory or smell, textural, or light stimulation, although other types of stimulation may be employed. In some embodiments, the stimulus is delivered via the sensor, although the stimulus may be delivered via other methods as this aspect of the disclosure is not limiting. A skilled artisan should appreciate that more than one stimulus (whether simultaneous or sequential) may be applied to a single animal during the course of an experiment. A person having skill in the art should further appreciate that different stimuli may be applied to each of the animals in a study when multiple animals are being tested.

In some embodiments, light stimulus may be delivered through the surface of the panel or sensor. For purposes herein, light stimulus may include the application of light to stimulate a genetically engineered, light sensitive animal and the application of light as a visual stimulus for any animal. For example, light stimulus may be applied by directing specific wavelengths of laser generated light at points on the animal body (e.g., the footpads) using a scanning mirror galvanometer or other laser pointing devices, or via LED arrays positioned below the sensor and generating specific light wavelengths directed through the sensor to the entire inferior surface of the animal body. Light stimulus also may be applied via LED arrays generating specific wavelengths of light that can be positioned to generate FTIR of light that is then delivered to the surfaces of the rodent body in contact or nearby the sensor. Without wishing to be bound by theory, delivery of light using these methods may permit control of specific peripheral nerve activity or cell function using light as stimulus while simultaneously imaging the mouse to acquire and analyze behavior data related to the light-activated nerve or cell activity. For example, light stimulus can be used for the manipulation of genetically encoded light-sensitive proteins to study function of molecules, synapses, cells and system or other light sensitive molecules engineered to interact or bind to cellular proteins. Also as an example, the expression of naturally occurring light-gated proteins (e.g., channelrhodopsins) or the introduction of light sensitive molecules in defined subsets of cells or proteins can address important questions about cells and systems into which they are introduced since they allow cellular activity, such as the activation of specific cell types or the opening of specific ion channels, to be performed in a targeted manner by the administration of light. Also, a chemical that binds to proteins and makes them light sensitive may be used. The applied light may be applied in different temporal patterns, different sizes and intensities for different durations in order to activate or inhibit specific neurons, proteins or receptors.

In some embodiments, the surface temperature of the sensor may be manipulated to explore behavioral responses to a thermal stimulus. In some embodiments, the glass or panel may have a thermally conductive layer or a thermally conductive plate may be used. The temperature also may be varied via an infrared heat source or via an infrared light source. In some embodiments, the temperature may be manually adjusted whereas in other embodiments it may be automatically adjustable. In some embodiments, the surface upon which the animal is freely roaming may have one or more textures to stimulate the animal.

Figure 2:
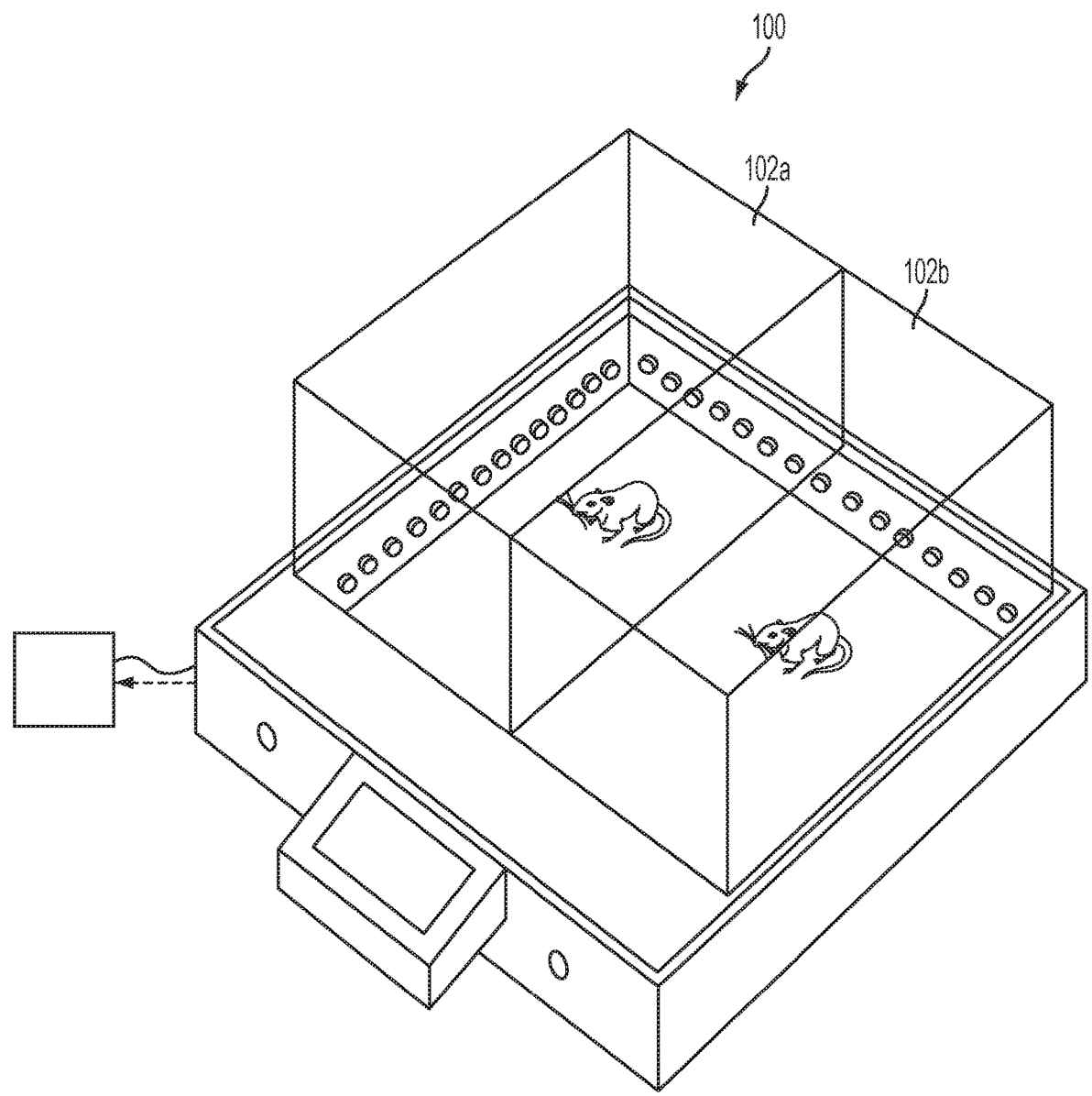
FIG. 2 is a perspective view of a device for monitoring animal behavior according to one embodiment.

Turning now to the figures, FIG. 1 shows a device 100 for monitoring animal behavior according to one embodiment. In some embodiments, monitoring animal behavior via the device 100 includes detecting and recording animal behavior. The device 100 includes a corral 102 defining a contained field within which a rodent 104 may be housed during a study. As shown in this figure, the corral 102 is an open field which allows the rodent 104 to freely move. Although only one corral 102 is shown in the device 100 of FIG. 1, the device 100 may have multiple corrals 102 in other embodiments. For example, as shown in FIG. 2, the device 100 may have two corrals 102a, 102b, each of which is shown to house a rodent 104 during a laboratory experiment. A person having skill in the art should appreciate that device 100 may have more than two corrals 102a, 102b in other embodiments, as this aspect of the disclosure is not limited in this regard. For example, the device 100 may have 6, 8, 10, 12, or even 20 corrals in other embodiments. A skilled artisan also should appreciate that although only one rodent 104 is shown in each of the corrals illustrated in FIGS. 1 and 2, the device 100 may conduct experiments with more than one rodent 104 per corral. For example, depending on the size of the corral 102 and on the experiment being conducted, each corral 102 may house 2, 4, 6, 8 or more rodents 104. A person having skill in the art should appreciate that each corral need not house the same number of rodents. For example, in one embodiment, a first corral 102a may house one rodent 104, while the second corral 102b may house more than one rodent 104. Without wishing to be bound by theory, by having a device configured to allow multiple rodents 104 to be housed in the same corral, and to monitor the behavior of each of the freely moving rodents 104, experiments relating to the social interactions, e.g., social anxiety, of the rodents 104 may be conducted.

Each corral 102 in the device 100 may be used to conduct separate experiments. Additionally, although the device 100 may conduct the same experiment in all of the corrals 102, in some embodiments, the device 100 may conduct different experiments in each corral 102. The device 100 also may be configured such that all the corrals 102 begin the experiment at the same time, although the device 100 may be configured such that the experiment being performed in each corral 102 begins at a different time. This may improve consistency in the testing, e.g., by allowing all the experiments to begin after the same amount of time has passed after each rodent has been genetically modified or stimulated instead of starting the experiments after different periods of time have passed.

In some embodiments, additional "dummy" corrals that are identical to the corrals 102 shown in FIGS. 1 and 2 are used to allow a first mouse (or group of mice) to be habituated to the test conditions while a second mouse (or group of mice) is being tested in the corrals 102.

Although the corrals 102 in FIGS. 1 and 2 are shown having a transparent upper enclosure 106, thus allowing observation of the rodents 104 from above the device, a person having skill in the art should appreciate that all or portions of the upper enclosure 106 also may be opaque. In some embodiments, the upper enclosure 106 includes black walls that prevent observation and light penetration via the top and sides of the upper enclosure 106.

As shown in FIG. 1, the device also includes a base surface 108 on which the rodents move and which is sensitive to the rodent's 104 paw print, toe print, or other inferior surface of the rodent. As shown in FIG. 1, the base surface 108 may be a transparent surface which allows observation of the rodent from below the device 100. For purposes herein, a transparent/clear surface may include a surface capable of allowing visible and/or non-visible light to pass therethrough. In some embodiments, the base surface 108 is the sensor of the device 100.

Figure 3:
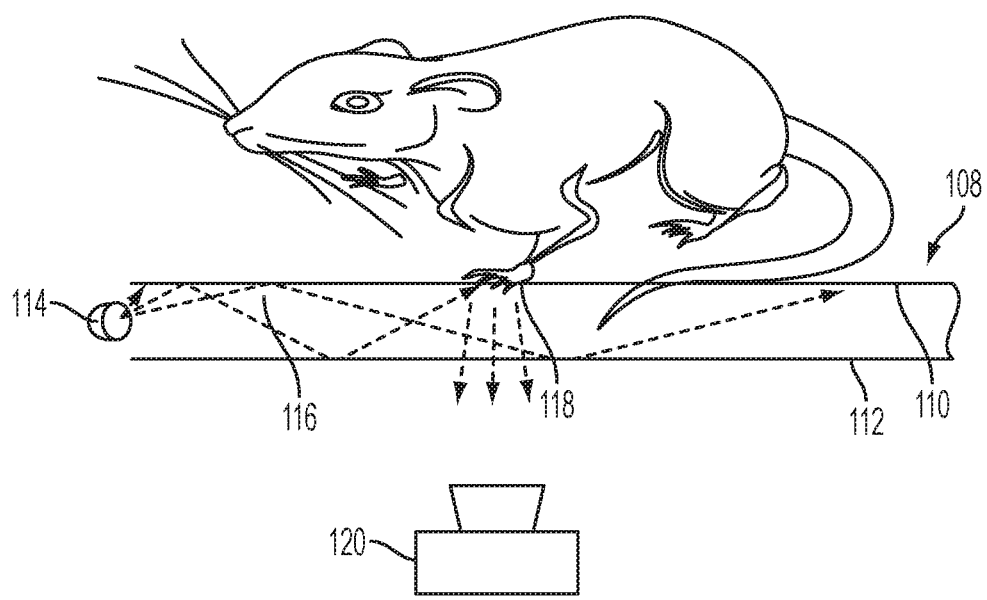
FIG. 3 is a cross-sectional side view of a base surface of a device for monitoring animal behavior according to one embodiment.

As shown in FIG. 3, the base surface 108 includes an upper base surface 110 and a lower base surface 112. In some embodiments, the base surface 108 is a glass, acrylic, or silicone material, although other suitable materials may be used as this aspect of the disclosure is not limited in this regard. In some embodiments, all or portions of the upper base surface 110 includes a textured surface which acts as a stimulus for the rodent(s) 104 in the corral 102.

As shown in FIGS. 1-3, lights 114, such as LEDs, are positioned around the perimeter of the base surface 108. In some embodiments, the lights 114 are mounted in a channel (not shown) within a movable rail. In such embodiments, the lights 114 and base structure 108 (e.g., a glass FTIR surface) may be easily separated for replacement of broken parts and to allow for optimal positioning of lights relative to an edge of the surface 108. In other embodiments, the lights 114 may be positioned as strip lights around the edge of the surface 108.

The lights 114 emit light which may include a non-visible band light, e.g. near-infrared, infrared, or ultraviolet light, or another suitable type of light. As shown in FIG. 3, the light emitted by the lights 114 is totally internally reflected (see e.g. at 116). When a rodent's 104 footprint, toe print, or other inferior surface comes into contact with the upper base surface 110, e.g. at 118, the internally reflected light becomes frustrated and is refracted out of the base surface 108 via the bottom base surface 112.

The device 100 also may include a light source beneath the sensor or panel to facilitate illumination of the inferior surfaces of the animal not in contact with the sensor. This lighting may be positioned beneath the sensor or panel in a location outside the perimeter of the chamber footprint to facilitate lighting of the subject animal within the chamber while keeping the light source or reflections thereof away from the view of a camera or imaging device, e.g., a capturing device 120.

In some embodiments, rodents (e.g., mice) are more active when the corral 102 is illuminated with a red or infrared lights, which are not visible to the rodents, than when the corral 102 is illuminated with a white light (e.g., a visible light). In such embodiments, the mice also may act more naturally when the corral is illuminated with red or infrared light. Without wishing to be bound by theory, mice are naturally active only when it is dark and remain dormant when it is light. Again, without wishing to be bound by theory, when mice are forced into a brightly illuminated space they show signs of stress. It was hypothesized that mice would become more active and behave more naturally when confined to a corral with little to no visible light, instead of a conventional brightly lit corral, and in one embodiment, it was observed that mice in a dark corral are active for a longer period of time than mice in a lit environment.

Figure 4:
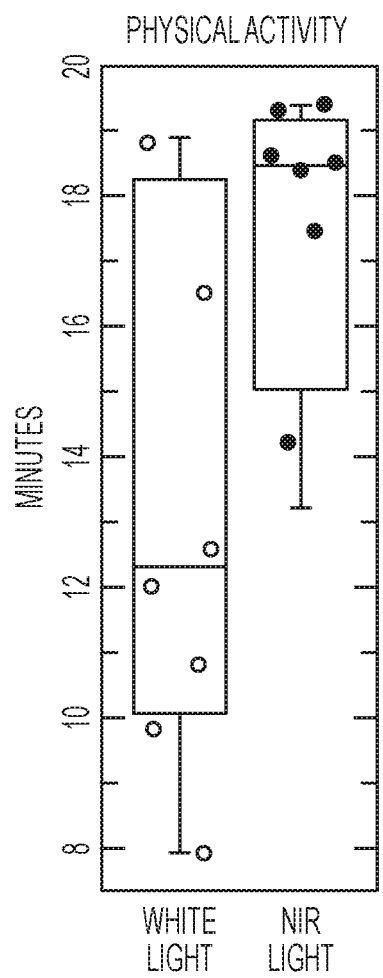
FIG. 4 is a graph showing a physical activity of mice in corrals lit by white light and by non-visible near infrared light.

For example, as illustrated in the graph in FIG. 4, when mice were observed for twenty (20) minutes in a translucent FTIR corral 102 illuminated from all sides with white light, the mice were physically active (e.g., walking, rearing, and grooming) for 13.41 minutes. In contrast, when the mice were placed in an opaque (e.g., "blackout") corral and were illuminated from below with only non-visible near infrared (NIR) light, the mice were physically active 19.39 of the 20 minutes.

Figure 5:
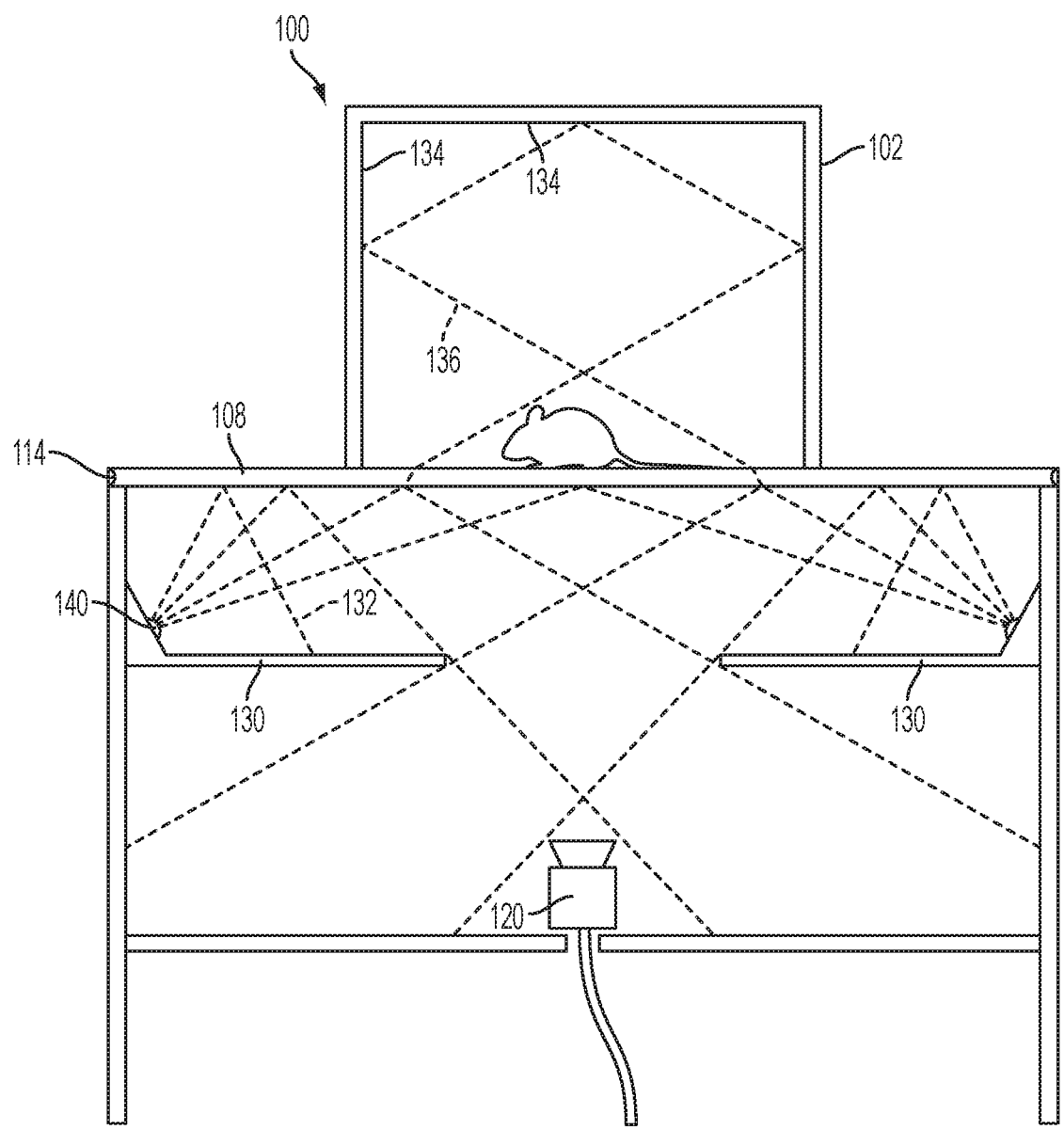
FIG. 5 is a cross-sectional side view of a device for monitoring animal behavior according to another embodiment.
Figure 10:
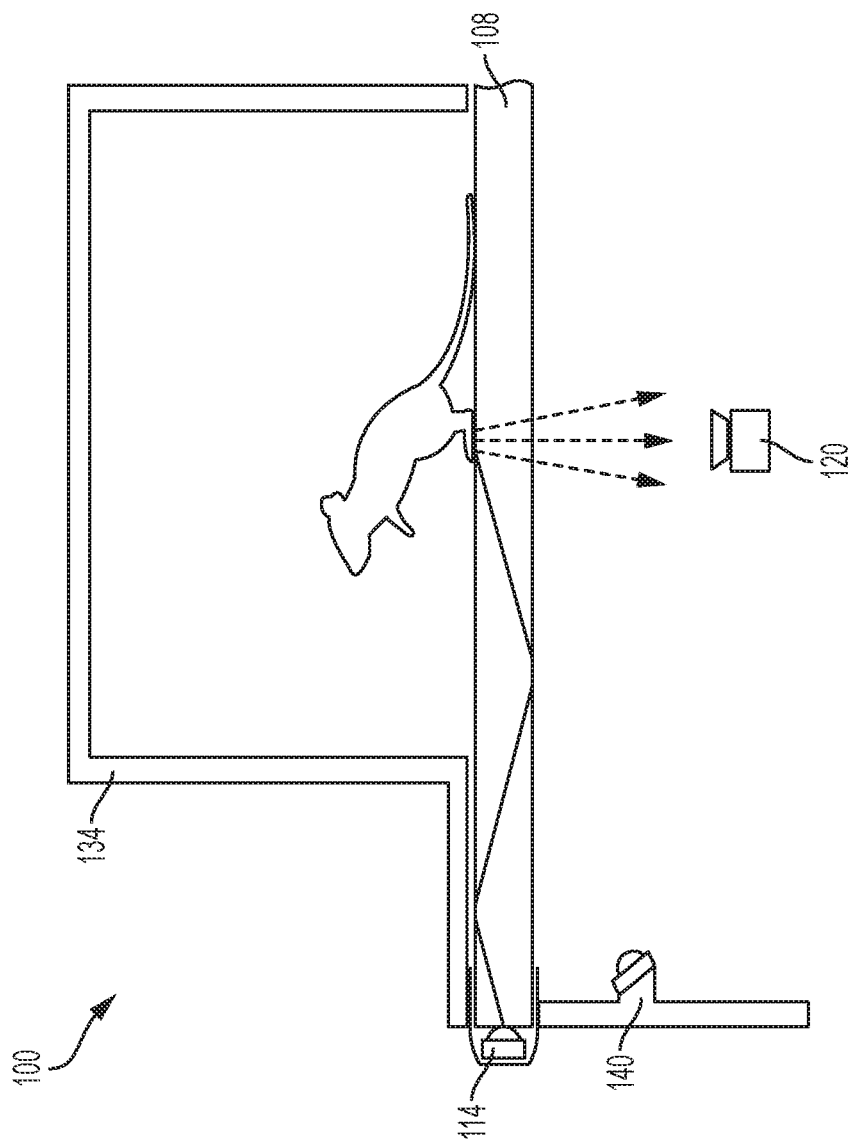
FIG. 10 is a cross-sectional side view of a device for monitoring animal behavior according to another embodiment.

Without wishing to be bound by theory, analyzing data illuminated from only FTIR-generated lights can be difficult because the feature being illuminated (e.g., the animal's hind paw) is not always readily identifiable. Applicants have realized that by illuminating the animal to identify the feature, in addition to illuminating the feature with FTIR-generated lights, improve behavioral analysis of the animal may be achieved. In some embodiments, as shown in FIGS. 5 and 10, a secondary light source, such as lights 140, may be used to illuminate the animal from beneath the surface 108, with the first light source 114 projecting FTIR-light into the surface 108. As will be appreciated, although the lights 140 are shown below the animal in this figure, the secondary light source may be located in other suitable locations in other embodiments. In some embodiments, the secondary light source may be of uniform in color and intensity.

In some embodiments, the field of view beyond the animal (e.g., rodent) may be illuminated with the secondary light source. In other embodiments, as will be described, the device is configured and the animal is staged such that a uniform black background is generated for capture by the capturing device, with only the subject being illuminated. In such embodiments, a reflective black background may be used for the surfaces that comprise the field of view beyond the subject. Such a configuration and makeup may generate a field of view beyond the subject that is without apparent illumination (e.g., a dark field of view).

In some embodiments, to optimize data, a light configuration from the secondary light source may be arranged such that the field of view beyond the subject appears dark. For example, the light emitted from the secondary light source may be entirely reflected away from the camera, as shown in FIG. 5, for example. In such embodiments, the reflections of the light are not visible because the sides of the corral are positioned such that all the light is reflected away from the cameras, except for the light that hits the animal. Such a configuration may create the appearance of a black background, even when the lights of the secondary light source are very bright and the surfaces are mirrors.

In some embodiments, to optimize the data, a lighting configuration from the secondary light source may be used to dimly illuminate the head, body, tail and paws to provide visual cues as to the identity and position of the FTIR-generated signal. Dim lighting may permit a freely behaving animal to be uniformly illuminated without generating any visible light or reflections of light in the field of view beyond the animal from the viewpoint of the capturing device. As will be appreciated, visible light may otherwise serve as a stimulus for the animals and disrupt the testing. In contrast dim lighting with little to no visible reflections limits the amount of stimulus to the animal.

As shown in FIG. 5, the capturing device 120 (e.g., a camera) is positioned below a transparent base surface 108 of the corral 102 and an opaque divider 130 is positioned between the corral 102 and the capturing device 120. The divider 130 may have a cutout that permits full view of the corral base surface 108 from the capturing device 120, while the field of view beyond the corral 102 is occluded. In some embodiments, the surface finish of the opaque divider 130 is matte to minimize secondary reflections. The lights 140 may be positioned so that the capturing device 120 is shadowed from rays of light 132 reflected off of lower base surface 112 of the corral base surface 108. To prevent illumination of the interior surfaces of the corral 102 from the viewpoint of the capturing device 120, the corral walls and/or ceiling (collectively, 134) may be constructed from an opaque material with a reflective surface and may be positioned so that reflected light rays 136 exiting the corral 102 are reflected away from the aperture of the capturing device 120.

While lighting the animal from beneath may inform a detection algorithm of the relative positions and identify one of the head, body and tail of the animal, this added light also may reduce the dynamic range (e.g., the fidelity) of the FTIR signal, and thus, limit its utility. For example, when the second light is turned on to identify a feature (e.g., a paw) of the animal, it may be difficult to determine when, and the extent to which, that feature (e.g., the paw) makes contact with the sensor. That is, when both the first and second lights are turned on, the changes in luminesce caused by different pressures being exerted by the paw on the surface may be more difficult to discern. For example, in some instances, the luminescence for the feature (e.g., the paw) may appear to be the same or nearly the same throughout. In contrast, with only FTIR illumination, the timing of this event, and the extent to which the paw is making contact, is obvious because the variations in luminescence are clearly visible.

Applicants have recognized that by using different lighting schemes to generate images of the body for feature identification and images of the footprint for visualizing changes in luminescence caused by different pressures being exerted by the feature (e.g., the paw), various advantages may be realized. For example, in one embodiment, the secondary light source may be turned on to illuminate the body for feature identification and then turned off, leaving only the first lights (the FTIR illumination) on to visualize changes in luminescence when the feature makes contact with the base surface. As will be appreciated, lighting schemes also may be used in which the secondary light source is alternated between dim and bright lights. For example, a bright light may be used to illuminate the animals feature, after which point the secondary light source is dimmed again. As will be appreciated, such a dim light may remain on when the FTIR illumination is used to illuminate the animal's paw print.

In some embodiments, to maintain the full dynamic range of the FTIR signal, the under lighting (e.g., the secondary light source) may be turned on only on alternating or for intermittent video frames. For example, the light may be turned on when a first video frame of the body is capture and then turned off when a second video frame showing the change in luminescence is captured. The lights below the animal also may be turned on and then turned off for intermittent periods of time that are not necessarily cued by the video frames. For example, the image capturing device may capture a video in which the under lighting is intermittently turned on and off. As will be appreciated, in such embodiments, the same outcome may be accomplished, with either a global shutter video camera or a camera with a rolling shutter. In some embodiments the underlighting may be NIR LEDS, although other suitable light sources may be used.

In some embodiments, this illumination strategy may permit recording of separable data streams of the same animal behavior from one capturing device 120 (e.g., a video camera), with one data stream being used for dynamic range of FTIR-generated foot position data and the other being used for orientation and analysis of body position. For example, as shown in FIGS. 11A-11B, paired videos can be captured, one showing the body form of the animal and the other showing the contact areas of the paws. FIG. 11A illustrates visualization of the paws, tail and body of mice. FIG. 11B uses only FTIR illumination to reveal the differences in contact luminance that correspond the relative weight borne by each of the paws and within each paw.

According to one aspect, the paired videos may be sequentially and comparatively analyzed by machine vision algorithms to reveal objective, highly sensitive readouts of voluntary mouse behavior and its disturbances. For example, the raw data recorded from the image capturing devices may be used to extract the orientation, body contour, foot position and foot identities. First, as shown in FIG. 11C, a machine vision algorithm may be used to analyze the illuminated frame of FIG. 11A to identify the position and identity of the tail and paws.

Figure 15:
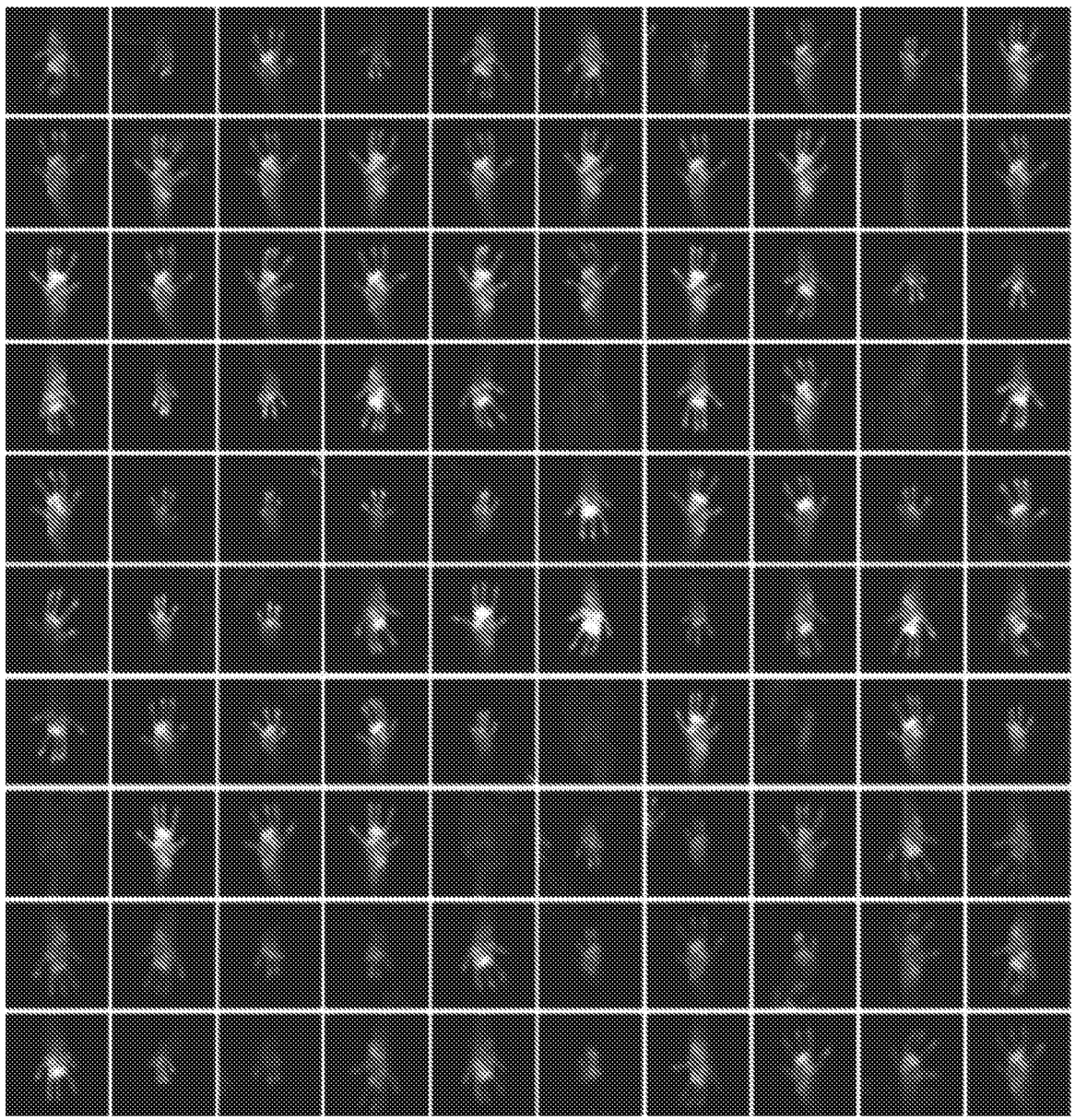
FIG. 15 is an illustration of paw images extracted from video frames using machine vision algorithms.

Without wishing to be bound by theory, in some embodiments, such machine vision algorithms are trained to identify and extract images of paws and tails by manually labelling these features on thousands of video frames of ventrally illuminated mouse videos. Using these trained algorithms, a pattern recognition code may be developed for extracting paw images from still video frames. For example, FIG. 15 illustrates a computer-assisted extraction of paw images from video frames using a trained vision algorithm.

In some embodiments, the machine vision algorithms are also trained to identify the tail and tail base to allow for automatic determination of paw position. For example, such an algorithm may be used to identify the right-front, right-back, left-front and left-back paws of a rodent. Without wishing to be bound by theory, the tail and tail base may be used as a starting point to determine the animal's nose and body midline. From there, codes may be developed to determine in which quadrant—the front right, front left, back right and back left—the extracted paw belongs to based upon the position of the tail and tail base. For example, as shown in FIG. 11C, using the position of the rodent's tail and tail base, the algorithm has identified the illuminated features as being the animal's right hind paw ("hp") and left hind paw ("hp").

Once the specific paw regions have been identified using the ventrally illuminated frames (e.g., that shown in FIG. 11C), the luminance (e.g., the mean luminance) of these areas may be measured on the next video frame, which has features illuminated by only the FTIR lighting. Such a step is illustrated in FIG. 11D, which shows the luminance of the left and right hind paw areas being measured via the algorithm. As will be appreciated, these steps may be repeated for all frames (e.g., the paired frames) in a video to produce measurements of the animal's individual paw luminance over time. Such data may thereafter be used to analyze rodent behavior.

In some embodiments, the above-described algorithm may be used to simultaneously track and observe multiple behavior parameters of one or more freely moving subjects (e.g., rodents) for long periods of time. Such an algorithm may allow persistent tracking of a single foot (e.g., to which one treatment might be applied), but not to others, for the purpose of studying behavioral perturbation in animals.

As will be appreciated, experiments may include hundreds of mice, with data being collected over hundreds of hours. Without wishing to be bound by theory, manually scoring data to determine pain measurements may be mentally exhausting and may greatly limit the duration and reliability of data collected by an individual observer. As such, advantages may be realized by using the above-described algorithm, which automates the analysis of behaviors to generate a catalogue or inventory of all objectively-identified behaviors or actions exhibited by an animal.

Figure 16:
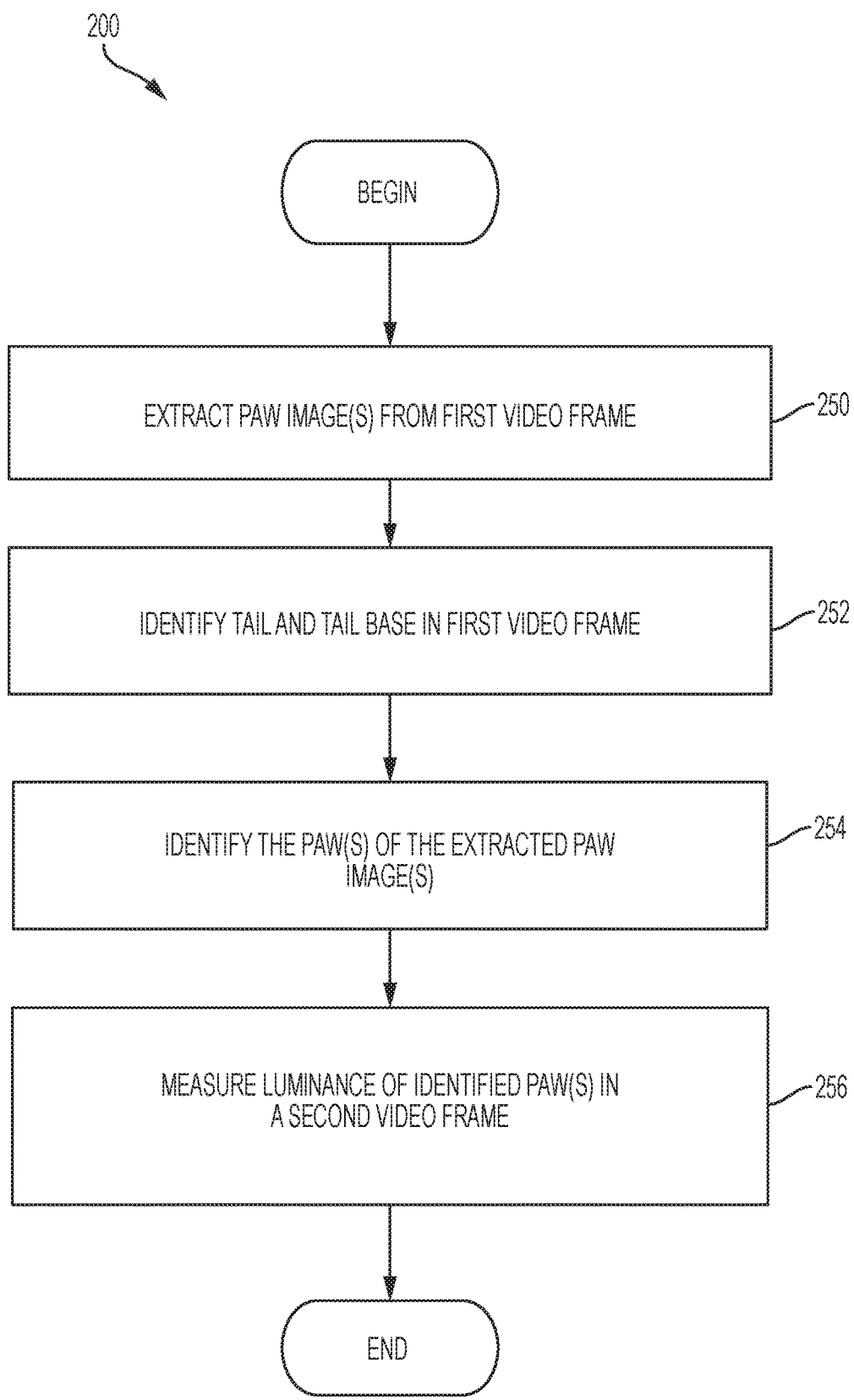
FIG. 16 is a flow chart of an illustrative algorithm used to gather measurements of paw luminance over time.

FIG. 16 shows a flow chart illustrating the algorithm 200 used to generate measurements of the individual paw luminance over time. In one embodiment, as illustrated in this figure, the algorithm 200 includes the step of extracting, in a first video frame illuminated with under lighting, images of an animal's paw or paws 250. Next, the algorithm identifies the animal's tail and tail base in the first video frame 252. Using the position of the tail and tail base to determine the animal's nose and body midline, the particular paw(s) in the extracted image from the first video frame may be identified 254. Next, the algorithm measures the corresponding luminance of the identified paw(s) in a second video frame illuminated by only FTIR lighting 256. These steps may be repeated for all frames in a video to produce measurements of the individual paw(s) over time.

In one embodiment, the device includes a switch that utilizes the "shutter" signal generated by the camera to identify the duration and timing of the video frames. A software-based counter is then employed to control the secondary light source beneath the animal, turning it on only for the duration of frame exposure of periodic subsequent video frames such as every other frame, every $10^{th}$ frame, every $100^{th}$ frame, or after another suitable number of frames. In some embodiments, video frames are taken 5 ms apart, 10 ms apart, 15 ms apart, although other suitable time delays may be used. In such embodiments, there may be 50 frames taken per second. There also may be 180 frames taken per second.

Although a second light source has been described for use in determining the relative identity and position of the animal's features, other suitable methods may be used. For example, in another embodiment, only the first, FTIR light source may be used to gather both the identity and position of the features and the contact luminescence. That is, for the first frame, a high intensity FTIR reading may be taken to show the relative position and identity of the rodent. Then, for a second frame, the typical FTIR reading, showing contact luminesce, is taken. A single light source also may be used to take all readings in embodiments having two different capturing devices (e.g., cameras), each with different filters—a first to view the position and identity and a second to determine the contact luminescence. Or a single capturing device (e.g., camera) may be used with the two noted filters.

In other embodiments, the position and identity of the animal's features may be done via another tracking method. For example, the animal may be tagged (e.g., an RFID tag or some other tag) and the device may include a sensor to track the position of the animal and capture FTIR-illuminated data when the animal has changed positions.

In other embodiments, the device may be configured to only save the data corresponding to the animal's features (e.g., the body, head, tail, footprint and/or toe print) and not to the entire environment (e.g., the corral). In such embodiments, after the environment has been illuminated, the relevant portions of data (e.g., the data showing images of the animal's footprint, toe print, body, tail, and/or head) are extracted, and the remainder of the data (e.g., images of the environment) is discarded. This data processing may occur after each illumination, after certain periods of time, or after the completion of an experiment. As will be appreciated, the data may be stored in a computer-readable storage medium.

As shown in FIGS. 3, 5 and 10 the capturing device 120 of the device 100 may be located below the lower base surface 112 for capturing the refracted light. In some embodiments, the capturing device 120 may be located in the housing 122 (see FIG. 1) of the device, although, in other embodiment the capturing device 120 may be separate from the device 100. The capturing device 120 may cooperate with the base surface 108 to capture a profile of the rodent's 104 full footprint, toe print when the rodent 104 is standing on its toes, or other inferior surface (e.g., the rodent's 104 abdomen).

In some embodiments, the capturing device 120 is a camera for recording the movement of the rodent or rodents. The camera may be a near-infrared camera in some embodiments, although other types of cameras may be employed as this aspect of the disclosure is not limiting. Without wishing to be bound by theory, the type of capturing device 120 corresponds to the type of band light emitted by the lights 114. For example, in embodiments in which a near-infrared band light is emitted by the lights 114, a near-infrared camera is used.

In some embodiments, the device 100 is configured such that images of the topographical features representing the inferior surface of each freely roaming rodent or rodents 104 in a single corral 102 may be separately analyzed. Without wishing to be bound by theory, the behavior of the rodent(s) 104 may be compared with either or both the behavior of other rodent(s) 104 in the same corral 102 and the behavior of any rodent(s) in other corrals 102.

Figure 6A:
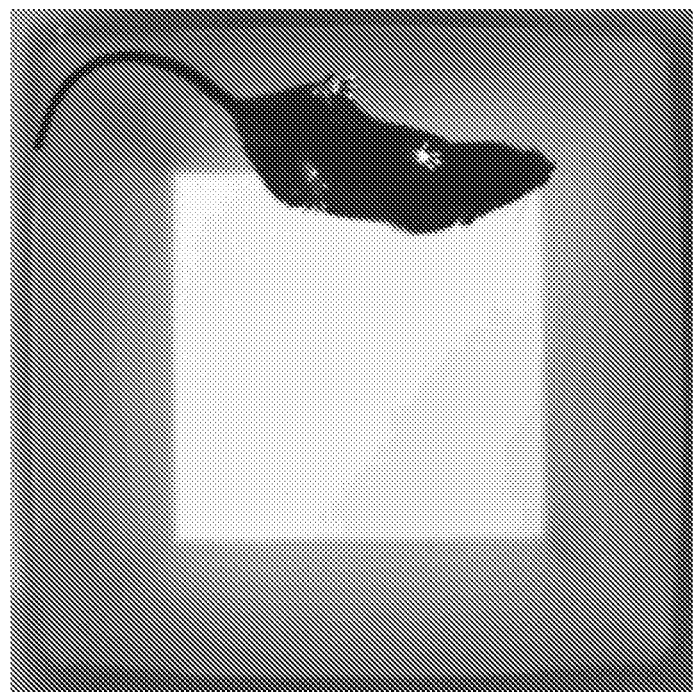
FIGS. 6A-6J are images representing screen shots of recordings captured by a capturing device according to various embodiments, each showing a rodent making contact with a base surface.
Figure 6B:
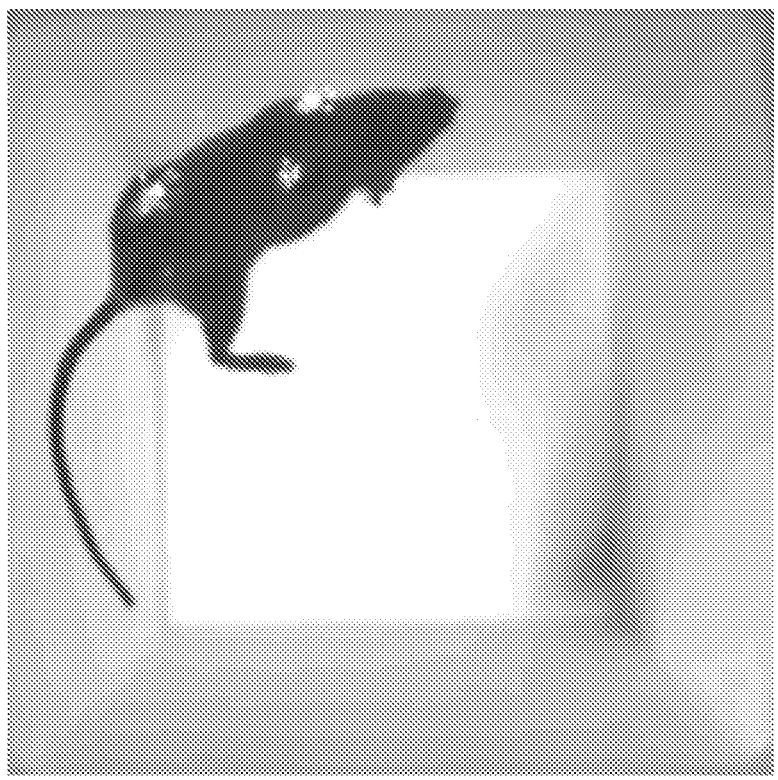
Figure 6C:
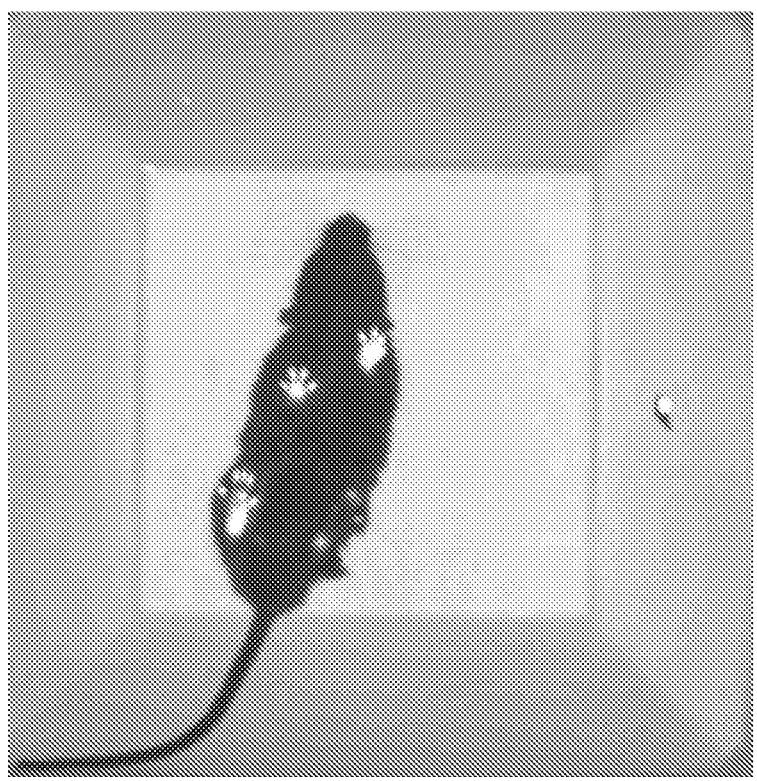
Figure 6D:
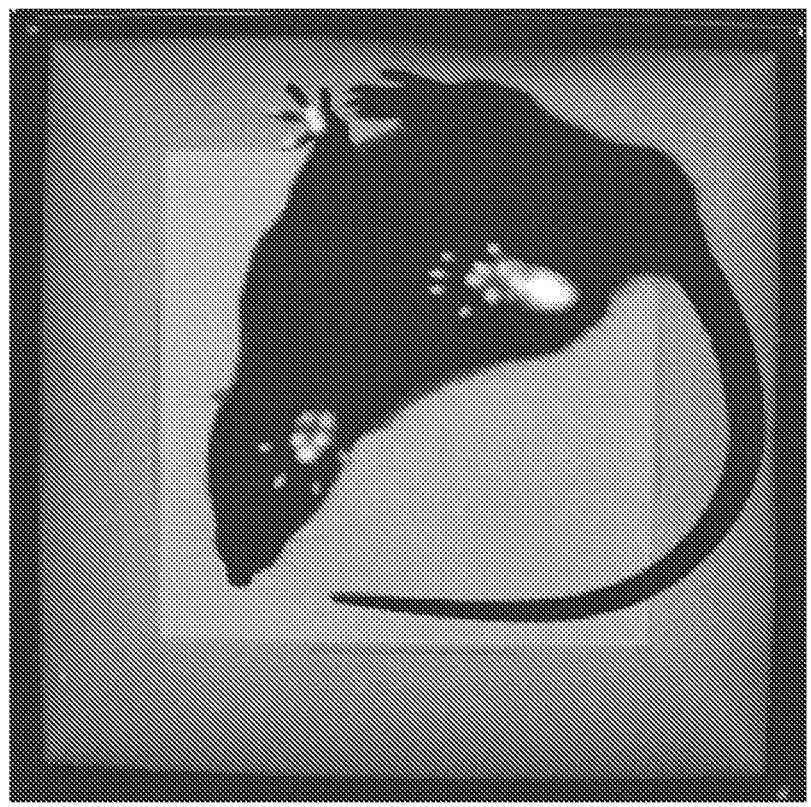
Figure 6E:
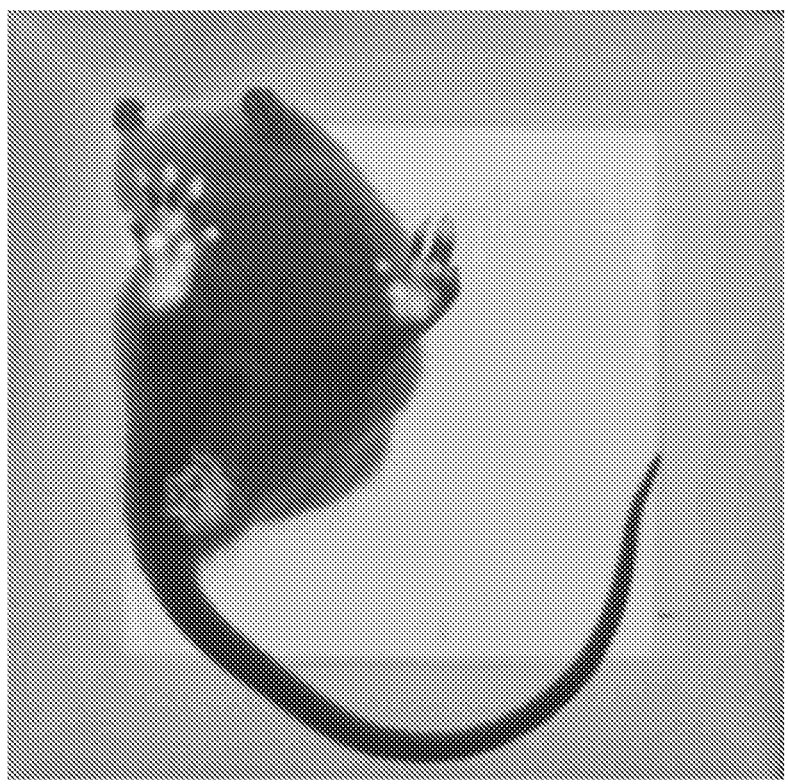
Figure 6F:
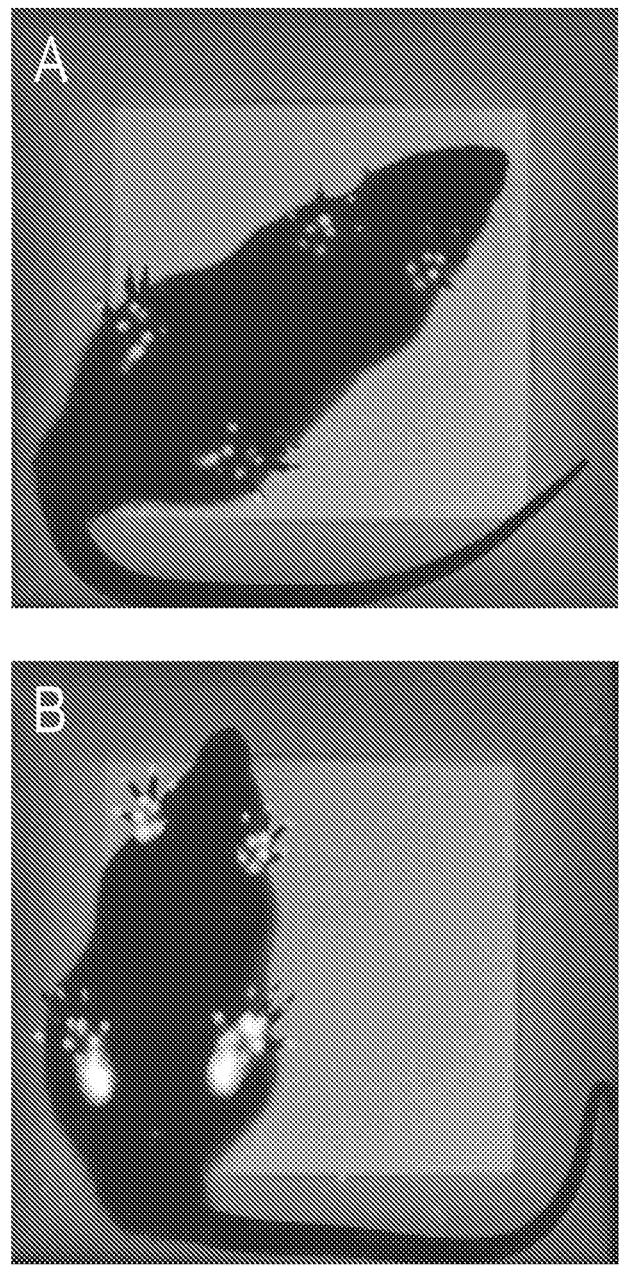
Figure 6G:
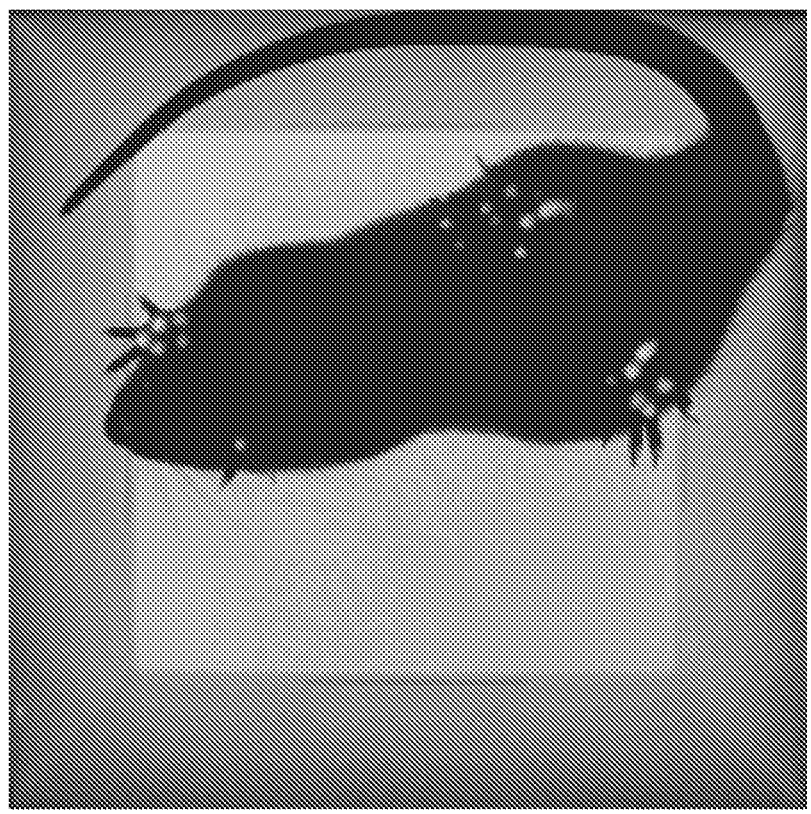
Figure 6H:
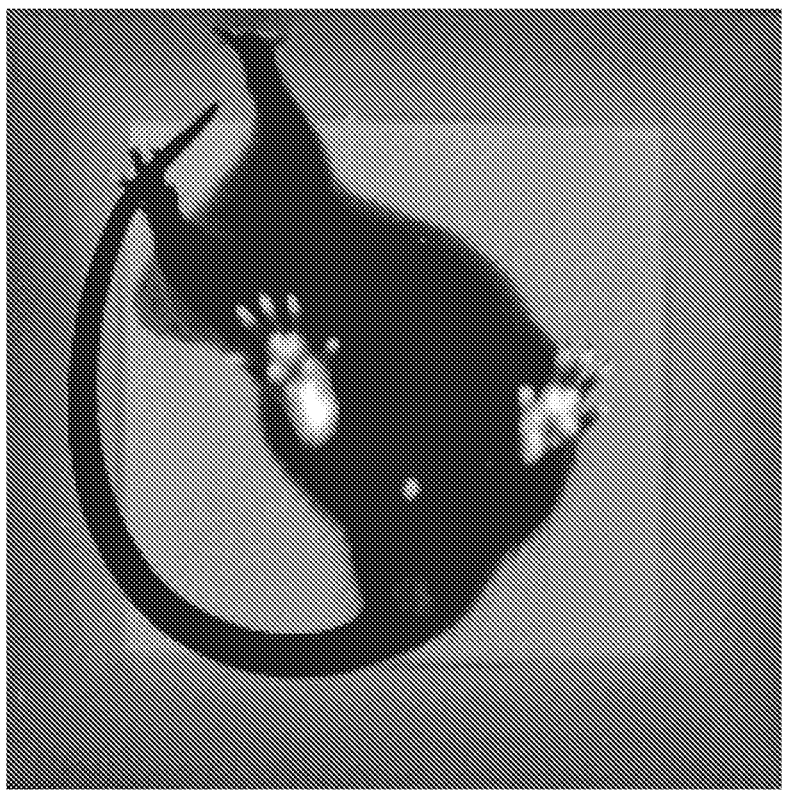
Figure 6I:
Figure 6J:
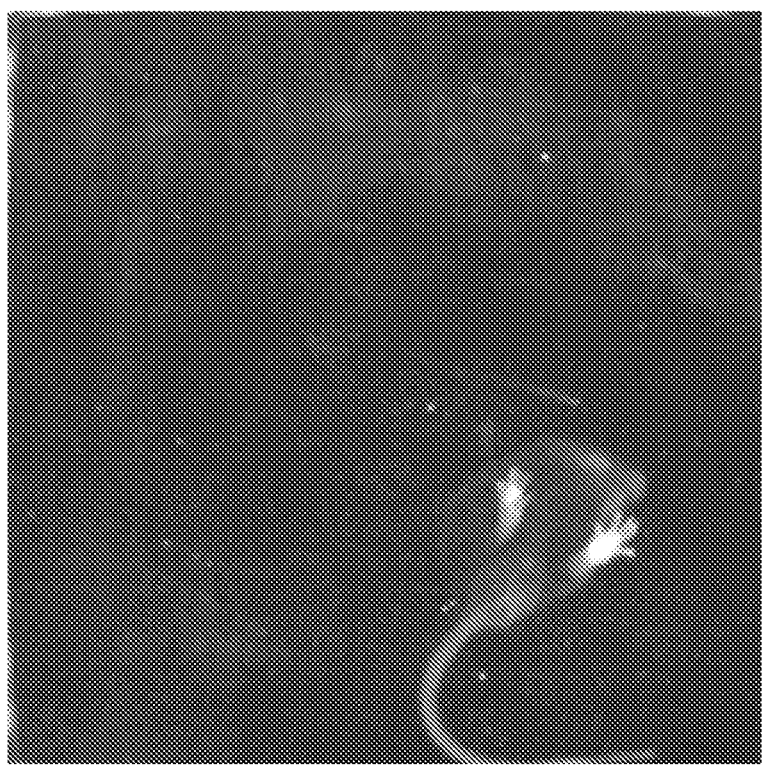

Examples of recordings captured by an exemplary capturing device can be seen in FIG. 6A-6J, which represent screen shots of the recordings taken by a video camera. FIG. 6A shows a Naïve mouse according to one embodiment. FIG. 6B shows the mouse of FIG. 6A twenty-four hours after a nerve injury. FIG. 6C shows the mouse of FIG. 6A twenty-one days after the nerve injury. FIG. 6D shows a Naïve rat according to another embodiment. FIG. 6E shows the rat of FIG. 6D twenty-four hours after an adjuvant-evoked injury to the rat's left hind paw. FIG. 6F illustrates how rats show increasing footprint irradiance upon habituation in an infrared-FTIR device enclosure. As shown in FIG. 6F, "tiptoeing" behavior often returns when an individual enters the room or upon loud noise such as clapping (e.g., handclapping). FIG. 6G illustrates a rat with no habituation. FIG. 6H shows the rat of FIG. 6G after twenty-minutes have passed. FIG. 6I illustrates FTIR in dark and underlit conditions. FIG. 6J shows spontaneous injuries that are detected in a Naïve mouse. These images reveal that rodents in a more relaxed state exhibit more full-foot contact as opposed to rodents in a more anxious state that exhibit substantially toe-only contact.

Figure 7A:
FIG. 7A-7B are images representing screen shots of recordings captured by a capturing device according to other embodiments, each showing a rodent making contact with a base surface.
Figure 7B:
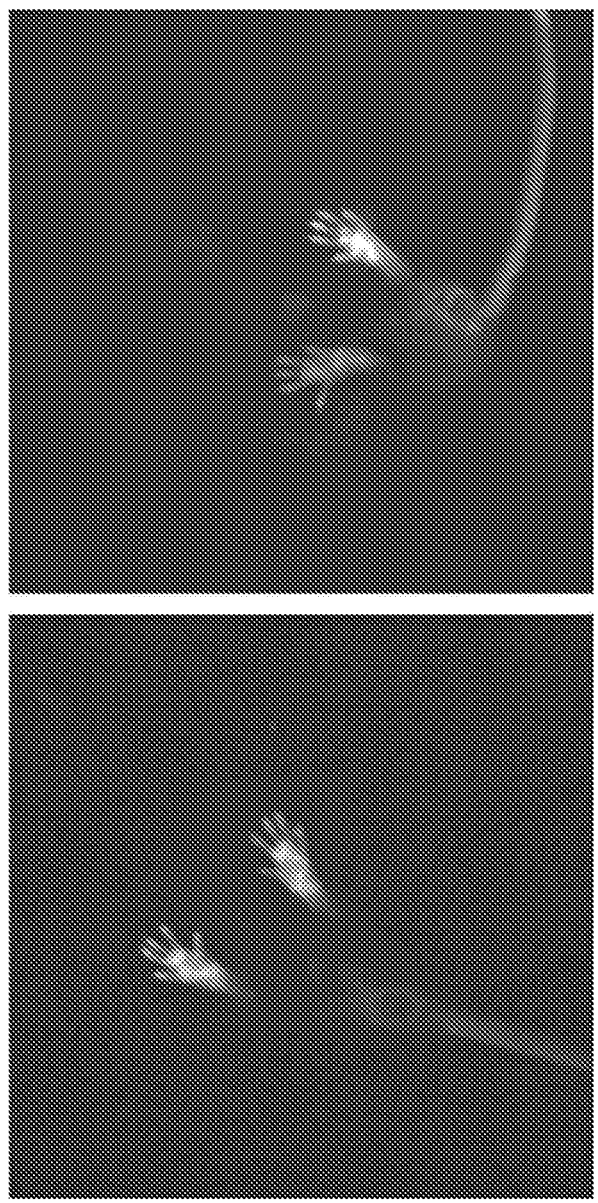

FIGS. 7A and 7B illustrate examples of FTIR recordings showing distinct pain-related behaviors in mouse models of abdominal pain and distinct pain-related behaviors when a mouse paw is injured, respectively. As shown in FIG. 7A at left, naïve mice walk with their weight shifted towards their hindpaws, which results in increased FTIR luminance of the hindpaws in this figure. In FIG. 7A at right, an embodiment showing abdominal pain, the mice shift their weight to their forepaws while walking. In such an embodiment, there is increased FTIR luminance of the forepaws as compared to that of the naïve mice shown in FIG. 7A at left.

FIG. 7B at left shows a naïve mouse standing on its hindpaws while grooming. In this embodiment, the luminance of each hind paw is substantially similar. When a mouse has been injured in a spontaneous fight with another mouse, for example, the location of injury is indicated by different FTIR luminance for each hind paw. As shown in FIG. 7B, at right, the mouse has an fight-related injury to its right hind leg above the knee joint, which causes a reduced FTIR luminance in the paw nearest the injured limb. Stated differently, in such embodiments, mice with a spontaneous leg injury shift their weight to the uninjured leg (which has a greater FTIR luminance).

Figure 8:
FIG. 8 are images representing screen shots of recordings captured by a capturing device according to another embodiment, each showing a rodent making contact with a base surface.

FIG. 8 illustrates examples of FTIR recordings that detect analgesic efficacy, with great sensitivity. FIG. 8 at left shows a mouse after an experimental induction of inflammation, and presumably pain, in its left hind paw. FIG. 8 at right shows a mouse that has underwent the same experimental induction of inflammatory pain in the left hind paw as the mouse in FIG. 8 at left, but has also been given an analgesic (e.g., diclofenac) before FTIR imaging. As shown in these embodiments, the mouse treated with the analgesic does not shift its weight to the uninjured leg like the mouse that was not treated with the analgesic.

FIG. 8 also demonstrates the capability of the device to detect not only the form of the contact areas of the paw, but also the relative pressures exerted within the contact areas of the paws (e.g., by showing the differences in light intensity). For example, the FTIR images are brighter in areas where there is greater relative pressure exerted by the hind paw than in areas where there is less relative pressure exerted.

Figure 13:
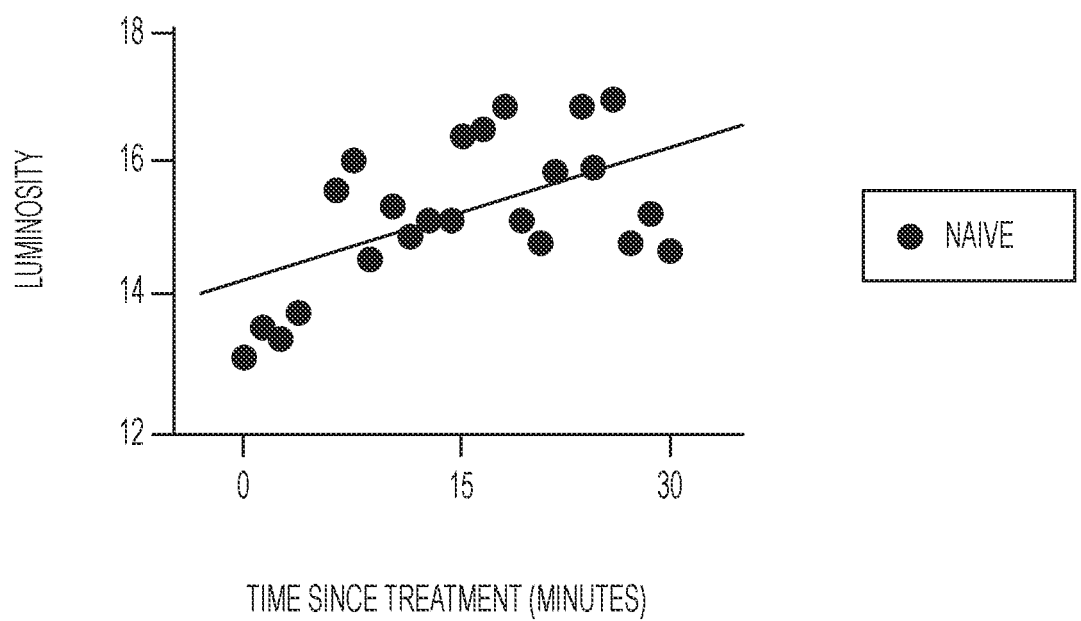
FIG. 13 illustrates mean paw illumination values of habituated, naïve mice 0-30 minutes after being placed in chamber.

FIGS. 12 and 13 illustrate data collected using first and second lights sources to measure differences in contact luminescence and to identify and locate the animal's features, respectively. For example, when naïve mice are first introduced to the chamber (i.e., immediately after being handled) they ambulate with the footpads, toes and keratin cuticles (toenails) of each paw extended. Only the cuticles, toe tips and small areas of the foot pads are in contact with the floor surface (i.e., on tiptoes), as shown in FIG. 12A. The tiptoeing is characterized by FTIR illumination as a dim, stippled appearance on the paw print. However, after 20 minutes of habituation to the device, the plantar surfaces of the paws become flattened, increasing the paw surface area in contact with the glass sensor (FIG. 12B). Upon introduction to the chamber on subsequent days, tiptoeing behavior ceases much sooner, typically within 5 minutes. Automatically scored data also reflect this increase in luminance over time (see FIG. 13, which shows mean paw luminance values). Notably, animals habituated to the device and walking flat-footed will resume tiptoeing when an investigator or handler enters the room. Similar behavior has been observed in response to a sudden loud noise, such as a door slamming. Considering the ecological position of mice as prey animals, and presuming investigators/handlers are perceived as a predator, tiptoeing in mice is interpreted as a measure of predation vigilance (i.e., an anxiety-related behavior).

FIG. 14A shows FTIR-generated paw luminance values 0-30 minutes after intraplantar injection of capsaicin (5 µl, 0.1%) to the left hind paw. FIG. 14B illustrates 180 minutes after injection of capsaicin to the left hind paw, mice again reveal periods of significantly increased luminance (weight bearing) in the uninjured (right) paw compared to the capsaicin-injected left paw. FIG. 14C illustrates that the luminance values of left and right hind paws are no different in naïve mice 0-30 minutes after being placed in chamber.

In some embodiments, the device 100 may include active or passive cooling elements to maintain the corrals at an appropriate temperature (e.g., to cool the corrals). For example, the corrals may include one or more openings for passive cooling (e.g., to allow air circulation). In another embodiment, the corral may include a fan mounted to the corral for active cooling. As will be appreciated, such active cooling may be used for long testing periods and behavioral recordings, as infrared lights may generate a lot of heat.

Turning back to FIG. 1, the device 100 also may have a control panel 124, such as a touch screen control panel, for controlling various parameters of the device 100, e.g. the stimulus applied in the corral 102. In some embodiments, the device 100 is connected to one or more control devices 126, which may be used to control the device 100. The control device 126 may be a computer (desktop or laptop), a tablet, a mobile device, or any other suitable apparatus for controlling the device 100. As shown in FIG. 1, the device 100 may be directly connected 128a to the control device 126 (e.g., via a USB connection) or the device 100 may be indirectly connected 128b to the control device 126. The indirect connection 128b may include an Internet, intranet, wireless, or other network connection suitable for indirectly connecting the control device 126 to the device 100. The control device 126 may run an application configured to store the images collected by the capturing device 120 and to process the images and/or convert the images into another data format for analysis. Other processing and/or analysis also may be performed by the device 100 itself and/or by the control device 126.

Figure 9:
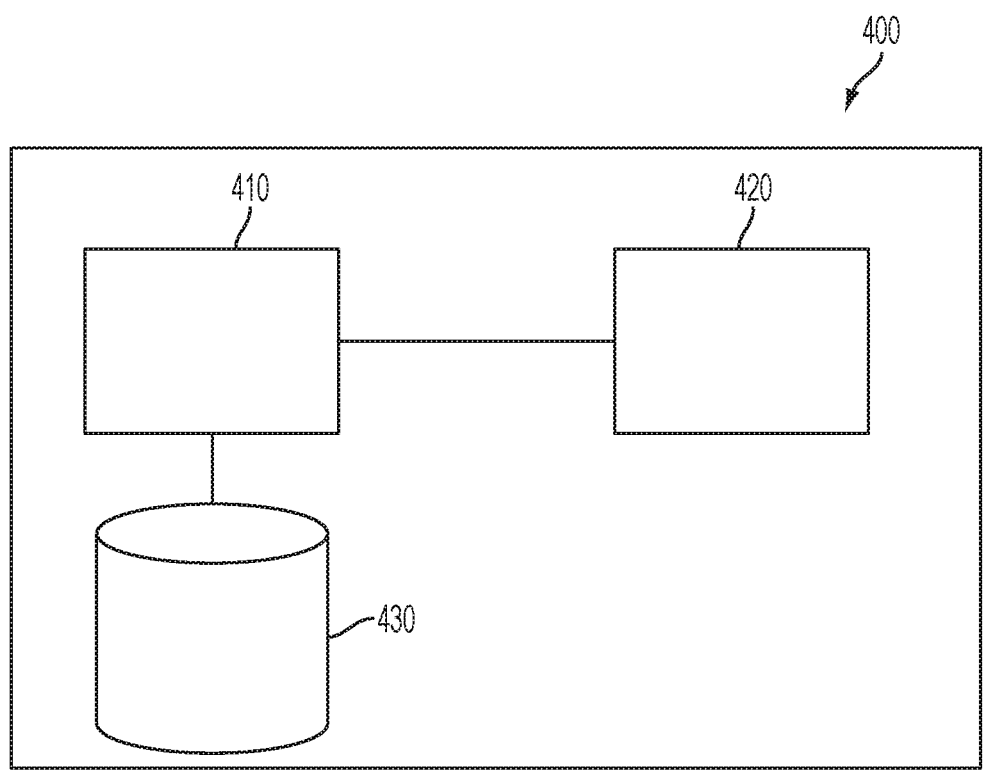
FIG. 9 is a schematic view of a computer system according to one embodiment.

The control device 126 in accordance with the techniques described herein may take any suitable form, as aspects of the present invention are not limited in this respect. An illustrative implementation of a computer system 400 that may be used in connection with some embodiments of the present invention is shown in FIG. 9. One or more computer systems such as computer system 400 may be used to implement any of the functionality described above. The computer system 400 may include one or more processors 410 (e.g., processing circuits) and one or more computer-readable storage media (i.e., tangible, non-transitory computer-readable media), e.g., volatile storage 420 (e.g., memory) and one or more non-volatile storage media 430, which may be formed of any suitable non-volatile data storage media. The processor(s) 410 may control writing data to and reading data from the volatile storage 420 and/or the non-volatile storage device 430 in any suitable manner, as aspects of the present invention are not limited in this respect. To perform any of the functionality described herein, processor(s) 410 may execute one or more instructions stored in one or more computer-readable storage media (e.g., volatile storage 420), which may serve as tangible, non-transitory computer-readable media storing instructions for execution by the processor 410.

In some embodiments, the control device (e.g., control system) is arranged to control the image capturing device to capture a first video frame in which at least one of a tail, body and head of the animal is illuminated by a light from below the animal and a second video frame in which both a profile of a full footprint of the animal and a profile of a toe print of the animal when the animal is standing on its toes is illuminated via a light that is totally internally reflected within the base surface. In some embodiments, the controller is also arranged to gather measurements of the luminance of the animal's full footprint or toe print over time by running the above-described algorithm. That is, the control system may run a module to extract a paw image and may then identify the paw based upon the position of the animal's identified tail and tail base. With the identified paw information, the control system may then measure the luminance of the identified paw. In some embodiments, the control system may also be arranged to save the identified paw information and the corresponding luminance information.

The above-described embodiments of the present invention can be implemented in any of numerous ways. For example, the embodiments may be implemented using hardware, software or a combination thereof. When implemented in software, the software code (e.g., instructions) can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (i.e., at least one tangible, non-transitory computer-readable medium, e.g., a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

In using the device 100, in one exemplary embodiment, at least a subset of a group of rodents is obtained and placed in one or more corrals 102 of the device 100. For purposes herein, a subset of rodents may include one or more rodents. In some embodiments, a first subset of rodents is placed in the corral 102 and isolated from another subset of rodents. In some embodiments, the rodents are genetically modified prior to placement in the corral 102. For example, the rodent may be optogenetically modified for manipulation of genetically encoded light-sensitive proteins to study the function of molecules, synapses, cells, and systems. There also may be proteins or other molecules given to the rodent. The device 100 may be enabled, either before or when the rodents are placed in the corral 102 such that the lights 114 emit band light which is totally internally reflected within the base surface 108.

Next, a stimulus may be applied to the rodents. In some embodiments, a light stimulus is applied by delivering a light through the base. The light stimulus may include different wavelengths of light and/or different patterns of light. In another embodiment, a thermal stimulus may be applied. For example, the base surface 108 maybe heated or cooled and/or the entire corral may be heated or cooled. In other embodiments, the rodents are subjected to pain stimulus. In some embodiments, the rodents 104 are subjected to different levels and types noises. The rodents also may be exposed to different smells. In some embodiments, multiple rodents are placed in the same corral to observe social interactions between the rodents. The applied stimulus may be delivered through the base surface 108 in some embodiments, although, in other embodiments, the stimulus may be delivered through alternate methods.

For devices performing a study using multiple rodents (whether in the same corral or in different corrals), the rodents may be stimulated with the same stimulus or with different stimuli. Additionally, the animals may receive only one stimulus or several different stimuli. The device 100 also may be configured such that the rodents are tested for short periods of time and/or for extended periods of time.

The behavior of the rodents, both before and after the stimulus, may be observed by imaging the spatial extent and intensity of signal of the footprint, toe print, and/or other inferior surface of the animal in response to the stimulus and its change over time. For example, in some embodiments, the rodents may get anxious and stand up on their toes creating a distinctive footprint, which differs from the more flattened footprint created when the rodents have settled down. The image is generated as a result of contact between the footprint or toe print, or other inferior surface of the rodent, and the base surface 108, which frustrates the band light and causes the light to be reflected and to exit the base surface 108 for detecting by the capturing device 120. The capturing device 120 captures the illuminated areas on the base surface 108 and these images are collected and analyzed.

In some embodiments, the capturing device may capture rodent behavior for short and/or long periods of time. For example, the capturing device may record rodent behavior for between about 10 seconds and 5 minutes. The capturing device also may capture images for between 5 and 10 minutes or even for more than 10 minutes. For example, the capturing device may capture rodent behavior for 20 minutes, 30 minutes, 40 minutes, an hour, 2 hours, or even up to 24 hours.

In some embodiments, a technician may be present the entire time that the capturing device is recording rodent behavior. For example, in one embodiment, the technician may be taking notes about the rodent behavior and/or may be operating the capturing device. In other embodiments, the device may be used without an investigator being present. For example, the technician may place the rodents in the one or more corrals and may walk away from the device during the testing period. In such embodiments, the rodents may continue to move within the one or more corrals, with the capturing device recording the rodent behavior. Without wishing to be bound by theory, when tests are performed without the presence of an investigator, the collected test data may be different than data collected when an investigator is present. For example, subjects (e.g., rodents), may behave differently when a human observer, or the odor of a human, is present within the experimental room, irrespective of whether the human can be seen by the rodent. As will be appreciated, the technician also may review the data captured by the capturing device from another room during the testing protocol or may review the data after the experiment has concluded and/or after the data has been processed.

Although embodiments have been shown and described as measuring the behavior of one or more rodents, it will be appreciated that the device also may be used to measure behavior of other animals (e.g., dogs and cats) or for humans. For example, the device may be sized so that an individual may stand or walk on the surface to analyze his or her gait. The device also may be used to analyze only a portion of an individual's body. For example, a smaller device may be used to analyze an individual's handprint when only an individuals' hand is placed on the surface.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A device for detecting and recording animal behavior, the device comprising:
    at least one corral defining a contained field, a base surface of the at least one corral being sensitive to a footprint of the animal; and
    an image capturing device cooperating with the base surface to capture a first video frame in which at least one of a tail, body and head of the animal is illuminated by a light below the animal and a second video frame in which both a profile of a full footprint of the animal and a profile of a toe print of the animal when the animal is standing on its toes is illuminated by a light that is totally internally reflected within the base surface;
    a control system arranged to control the image capturing device to capture the first and second video frames, the control system being further arranged to identify a paw in the first video frame and measure a corresponding luminance of the identified paw in the second frame.

2. The device of claim 1, wherein the control system identifies the paw in the first video frame by extracting a paw image from the first video frame, identifying a position of the tail and tail base, and determining the identity of the paw based upon the position of the tail.

3. The device of claim 2, wherein the identity of the paw is one of the right-front, right-back, left-front and left-back paw.

4. The device of claim 1, wherein the control system is further arranged to save the identified paw information and the corresponding luminance.

5. The device of claim 1, wherein, when the at least one of the tail, body, and head of the animal is illuminated by the light below the animal, a dark field is created above the animal.

6. A method of collecting behavior information of an animal, the method comprising:
    capturing a first image of at least one of a head, body and tail of the animal when the animal is illuminated with a first light;
    capturing a second image of both a profile of a full footprint of the animal and a profile of a toe print of the animal when a second light is totally internally reflected within the base surface to generate evanescent light between the footprint and the toe print of the animal and the base surface;
    identifying a first footprint in the first image; and
    measuring a corresponding evanescent light generated between the identified first footprint and the base surface in the second image.

7. The method of claim 6, wherein identifying the first footprint comprises:
    extracting an image of the first footprint from the first image;
    identifying a position of the tail of the animal in the first image; and
    determining an identity of the first footprint.

8. The method of claim 7, wherein determining the identity of the first footprint includes determining a quadrant in which the foot is located based upon a position of a nose and body midline of the animal as determined by the position of the tail.

9. The method of claim 7, wherein identifying the position of the tail includes identifying the position of the tail base.

10. The method of claim 6, further comprising saving the first footprint identity and the corresponding generated evanescent light.

11. The method of claim 6, wherein imaging both the footprint and the toe print of the animal comprises capturing the spatial extent of the contact, the weight born increasing intensity, and its change over time.

12. The method of claim 6, further comprising saving the first and second images.

13. The method of claim 12, wherein saving the first images comprises saving data of the at least one of the head, body and tail of the animal and discarding other remaining data.

14. The method of claim 12, wherein saving the second image comprises saving data of the both the profile of the full footprint of the animal and the profile of the toe print of the animal other remaining data.

15. The method of claim 13, wherein discarding other remaining data comprises discarding data of an environment of the animal.

16. The method of claim 8, further comprising, before capturing the first image, illuminating the at least one of the head, body and tail of the animal with the first light.

17. The method of claim 16, further comprising, before capturing the second imaging, turning off the first light.

18. The method of claim 6, where illuminating the at least of the head, body and tail of the animal with the first light includes illuminating the at least one of the head, body and tail of the animal from below the animal.

19. A device for detecting and recording animal behavior, the device comprising:
    at least one corral defining a contained field, a base surface of the at least one corral being sensitive to a footprint of the animal; and
    an image capturing device cooperating with the base surface to capture both a profile of a full footprint of the animal and a profile of a toe print of the animal when the animal is standing on its toes;
    wherein a first light is totally internally reflected within the base surface;
    wherein a second light illuminates at least one of a tail, body and head of the animal from below the animal.

20. The device of claim 19, further comprising a first light source for producing the first light.

21. The device of claim 20, further comprising a second light source for producing the second light.

22. The device of claim 20, wherein the first light source also produces the second light.

23. The device of claim 19, wherein the second light illuminates at least one of the tail, body and head of the animal from below the animal while a dark field is created above the animal.

24. The device of claim 19, wherein the image capturing device is arranged to capture an image of the at least one of the tail, body and head of the animal when the animal is illuminated with the second light.

25. The device of claim 19, wherein the image capturing device is arranged to capture an image of the profile of the full footprint of the animal and the profile of the toe print of the animal when the animal is standing on its toes when the second light is off.

\* \* \* \* \*